(12) United States Patent
Baker et al.

(10) Patent No.: US 10,795,973 B2
(45) Date of Patent: Oct. 6, 2020

(54) MEDICAMENT TRAINING DEVICE AND SYSTEM

(71) Applicants: Jeff Baker, Orlando, FL (US); Paul van der Pol, Winter Garden, FL (US); Craig Baker, Lebanon, OH (US); Mark Bunker, Orlando, FL (US); Seth Freytag, Winter Springs, FL (US); Karina Marulanda, Orlando, FL (US); Francis Michael Siemer, Orlando, FL (US); Matthew Palyo, Orlando, FL (US); Hou Shi Shuang, NingBo (CN); Christopher Chung, Orlando, FL (US)

(72) Inventors: Jeff Baker, Orlando, FL (US); Paul van der Pol, Winter Garden, FL (US); Craig Baker, Lebanon, OH (US); Mark Bunker, Orlando, FL (US); Seth Freytag, Winter Springs, FL (US); Karina Marulanda, Orlando, FL (US); Francis Michael Siemer, Orlando, FL (US); Matthew Palyo, Orlando, FL (US); Hou Shi Shuang, NingBo (CN); Christopher Chung, Orlando, FL (US)

(73) Assignee: NOBLE INTERNATIONAL, INC., Orlando, FL (US)

( * ) Notice: Subject to any disclaimer, the term of this patent is extended or adjusted under 35 U.S.C. 154(b) by 396 days.

(21) Appl. No.: 15/516,581

(22) PCT Filed: Oct. 5, 2015

(86) PCT No.: PCT/US2015/053992
§ 371 (c)(1),
(2) Date: Apr. 3, 2017

(87) PCT Pub. No.: WO2016/054634
PCT Pub. Date: Apr. 7, 2016

(65) Prior Publication Data
US 2017/0357776 A1    Dec. 14, 2017

Related U.S. Application Data

(63) Continuation-in-part of application No. 14/505,935, filed on Oct. 3, 2014, now Pat. No. 9,767,708.

(51) Int. Cl.
*A61M 5/32* (2006.01)
*G06F 19/00* (2018.01)
(Continued)

(52) U.S. Cl.
CPC .......... *G06F 19/3468* (2013.01); *A61M 5/32* (2013.01); *G09B 19/00* (2013.01);
(Continued)

(58) Field of Classification Search
CPC ... G06F 19/3468; G09B 19/00; G09B 23/285; G09B 19/0053; G09B 19/24;
(Continued)

(56) References Cited

U.S. PATENT DOCUMENTS 5,334,173 A    8/1994 Armstrong, Jr.
6,332,875 B2   12/2001 Inkpen et al.
(Continued)

FOREIGN PATENT DOCUMENTS

GB   2014145532515032 A   12/2014
WO        2014145535          9/2014

OTHER PUBLICATIONS

International Search Report and Written Opinion for PCT Application PCT/US15/053992 dated Jan. 7, 2016, pp. 1-29.
(Continued)

*Primary Examiner* — Amber R Stiles
(74) *Attorney, Agent, or Firm* — Timothy H. Van Dyke; Beusse, Wolter, Sanks & Maire PLLC

(57) ABSTRACT

In one embodiment, a medicament system configured to communicate information about a medicament device or about a use of a medicament device, or a combination thereof, to a user, is provided. The medicament system may include a medicament device including a housing, and a collateral device, wherein the collateral device may include an information detecting and/or receiving component configured to receive information from the medicament device and/or a sending component configured to send information to the medicament device, and optionally at least one of: a) a signal output component; b) a microprocessor; c) a storage medium component; and d) a power source, and wherein the medicament device may be configured to generate information detectable by the collateral device, or transmit information to the collateral device, wherein the collateral device may be configured to detect and/or receive information about the medicament device from the medicament device and provide information about the medicament device and/or a feedback about a use of the medicament device to a user of the system. The medicament device may further include a transmitter configured to communicate information and/or signals from the medicament device to the collateral device and/or a remote device, and/or receive information and/or signals from a collateral device and/or a remote device.

8 Claims, 23 Drawing Sheets

(51) Int. Cl.
*G09B 19/00* (2006.01)
*G09B 23/28* (2006.01)
*G09B 19/24* (2006.01)

(52) U.S. Cl.
CPC ....... *G09B 19/0053* (2013.01); *G09B 23/285* (2013.01); *G09B 19/24* (2013.01)

(58) Field of Classification Search
CPC .......... A61M 5/14546; A61M 5/14566; A61M 5/1458; A61M 5/32
See application file for complete search history.

(56) References Cited

U.S. PATENT DOCUMENTS

| | | | |
|---|---|---|---|
| 6,877,658 B2 | 4/2005 | Raistrick et al. | |
| 8,622,973 B2 | 1/2014 | Edwards et al. | |
| 2002/0165491 A1* | 11/2002 | Reilly | A61M 5/14546 604/154 |
| 2003/0229308 A1* | 12/2003 | Tsals | A61M 5/20 604/116 |
| 2005/0182358 A1* | 8/2005 | Veit | A61B 5/14532 604/93.01 |
| 2009/0212475 A1* | 8/2009 | Tropf | F16F 15/02 267/75 |
| 2012/0008811 A1* | 1/2012 | Edwards | A61M 5/2053 381/332 |
| 2013/0266919 A1 | 10/2013 | Baker et al. | |
| 2014/0276550 A1* | 9/2014 | Uram | A61M 5/1723 604/503 |
| 2015/0088092 A1* | 3/2015 | Holm | A61M 5/16831 604/506 |

OTHER PUBLICATIONS

Baker, J. Educating patients on self-administered drug injections, Pharm. Commerce, pp. 1-3 (2014).

\* cited by examiner

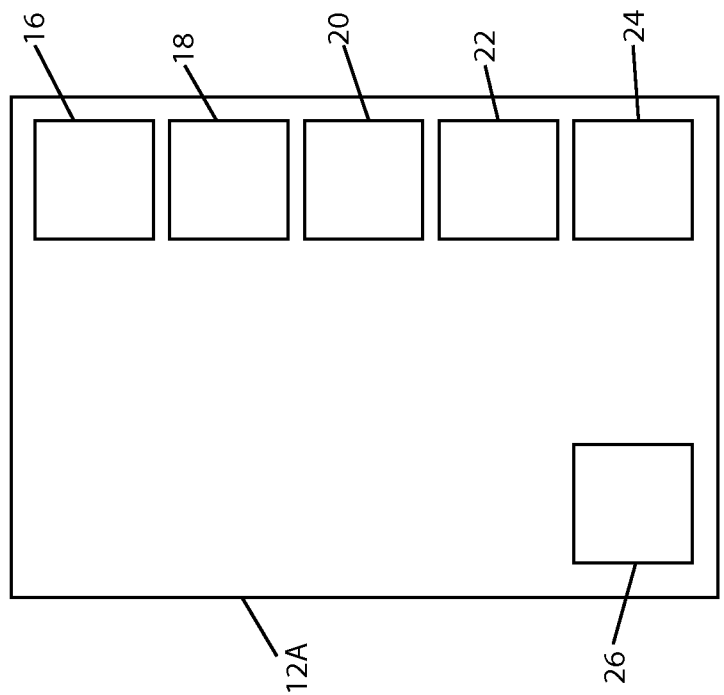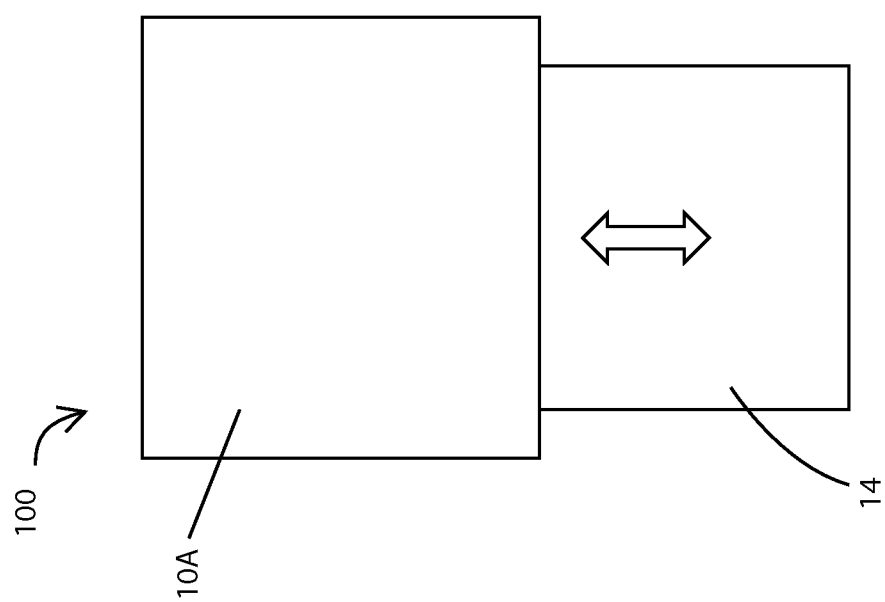
Fig. 1

MEDICAMENT TRAINING DEVICE AND SYSTEM

BACKGROUND

Performing a medical treatment or test on oneself carries with it certain risks and often creates a level of anxiety for the user performing the treatment or test. It has proven beneficial in the medical field to practice various medical techniques including drug delivery, specifically where it relates to injections and other invasive drug delivery means prior to delivering the medications to a patient in need, and particularly in the case of self-administration of medicaments. Training devices are helpful in reducing errors and anxiety associated with self administering medical treatment, as well as increasing efficiency and accuracy in providing the treatment to patients. Medical devices can be intimidating to use; the fear associated with giving oneself an injection, for example, can be traumatic. This fear is increased in persons with little or no experience in self-administration of medications. Consequently, devices and methods to assist in training individuals to inject themselves or otherwise self-administer medication are beneficial in decreasing or preventing the anxiety associated with medicament delivery. Medicament delivery training devices allow patients to practice giving themselves a full dose in a safe and effective manner.

SUMMARY

In one embodiment, a medicament system configured to communicate information about a medicament device or about a use of a medicament device, or a combination thereof, to a user, is provided. The medicament system may include a medicament device including a housing, and a collateral device, wherein the collateral device may include an information detecting and/or receiving component configured to receive information from the medicament device and/or a sending component configured to send information to the medicament device, and optionally at least one of: a) a signal output component; b) a microprocessor; c) a storage medium component; and d) a power source, and wherein the medicament device may be configured to generate information detectable by the collateral device, or transmit information to the collateral device, wherein the collateral device may be configured to detect and/or receive information about the medicament device from the medicament device and provide information about the medicament device and/or a feedback about a use of the medicament device to a user of the system. The medicament device may further include a transmitter configured to communicate information and/or signals from the medicament device to the collateral device and/or a remote device, and/or receive information and/or signals from a collateral device and/or a remote device.

In another non-limiting embodiment, a medicament system configured to communicate information about a medicament device or about a use of a medicament device, or a combination thereof, to a user is provided. The medicament system includes a medicament device including a housing, the medicament device including a sensor associated therewith, a transmitter configured to send information from the medicament device, and optionally at least one of: a) a signal output component; b) a microprocessor; c) a storage medium component; and d) a power source, the medicament system including a collateral device, the collateral device including an information detecting and/or receiving component configured to receive information produced from the sensor and/or a sending component configured to send information to the medicament device, a signal output component, a microprocessor, a storage medium component, and a power source, wherein the collateral device is configured to detect and/or receive information about the medicament device from the medicament device, and/or send information to the medicament device, and/or to provide information about the medicament device and/or a feedback about a use of the medicament device to a user of the system.

In yet another embodiment, a medicament system configured to communicate information about a medicament device or about a use of a medicament device, or a combination thereof, to a user, is provided. The medicament system includes a medicament device having a housing, a collateral device comprising a sensor, and an attachment component configured to secure the collateral device to the medicament device. The system may further include in an embodiment, a sending component configured to send information to the medicament device and/or the collateral device, an information detecting and/or receiving component configured to receive information from the medicament device about the medicament device and/or about a use of the medicament device. The system may further include a signal output component, a microprocessor, a storage medium component, and a power source, wherein the signal output component is configured to provide an output comprising information about the medicament system and/or information about a usage of the medicament device or system to a user of the system.

In another embodiment, a collateral device configured to receive information from and/or detect information about a medicament device is provided. The collateral device includes a collateral device housing, and may further include a detecting and/or a receiving component, wherein the detecting and/or receiving component is configured to detect information about or receive information from the medicament device, a signal output component configured to provide an output to a user, a power source, a microprocessor, and a storage module, wherein the collateral device provides a feedback to a user based on information detected and/or received by the detecting and/or receiving component, in a non-limiting embodiment.

In another embodiment, a method of using a collateral device to train a user of a medicament device to properly operate the medicament device to dispense a dose of medicament and to provide an instruction and/or a feedback to a user of the collateral device is provided. The method may include detecting and/or receiving information from a medicament device, processing information received from the medicament device, and providing a signal output to a user based on information received and processed.

BRIEF DESCRIPTION OF THE DRAWINGS

A more particular description briefly stated above will be rendered by reference to specific embodiments thereof that are illustrated in the appended drawings. Understanding that these drawings depict only typical embodiments and are not therefore to be considered to be limiting of its scope, the embodiments will be described and explained with additional specificity and detail through the use of the accompanying drawings in which:

FIG. 1 is a schematic of a system embodiment described herein.

DETAILED DESCRIPTION

Figure 2:
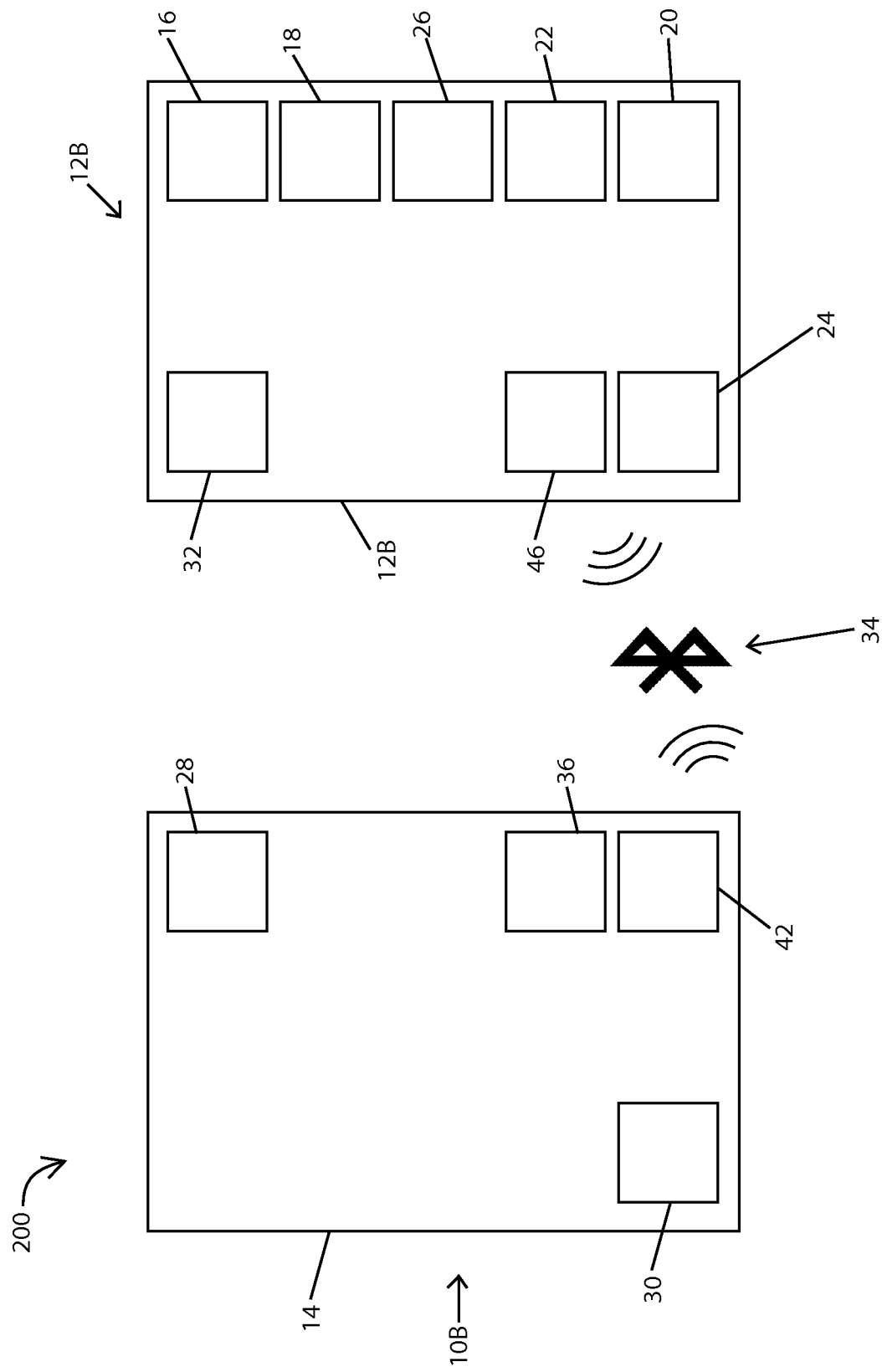
FIG. 2 is a schematic of another system embodiment described herein.

For the purposes of promoting an understanding of the principles and operation of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to those skilled in the art to which the invention pertains.

It is important to an understanding of the present invention to note that all technical and scientific terms used herein, unless defined herein, are intended to have the same meaning as commonly understood by one of ordinary skill in the art. The techniques employed herein are also those that are known to one of ordinary skill in the art, unless stated otherwise. For purposes of more clearly facilitating an understanding the invention as disclosed and claimed herein, the following definitions are provided. It should be borne in mind that all patents, patent applications, patent publications, technical publications, scientific publications, and other references referenced herein are hereby incorporated by reference in this application in order to more fully describe the state of the art to which the present invention pertains.

In addition to increasing confidence in self-administration in users by practicing with a medicament system, the inventors have identified additional benefits associated with multi-sensory learning regarding a medicament system. It has been discovered that multi-sensory learning establishes multiple pathways in separate areas in the brain and ultimately results in a highly effective learning experience. However, in order to gain benefits from multi-sensory learning devices, certain requirements must be met including but not limited to the following: the sources of stimuli must be in close proximity to one another; the sources of stimuli must be synchronous; the stimuli must be congruous semantically, otherwise the superior colliculus (area of the brain located in the midbrain known for integrating multiple sources of information) will segregate the stimuli instead of integrate them; and finally, the use of extraneous materials must be limited.

With knowledge of the essential factors in multi-sensory learning and incorporation of the multi-sensory learning features into a training system, the inventors have developed a novel, cutting-edge medicament system. The inventors have identified a need for a system to monitor users and their use of a medicament device, assist users in administering medication, or training for medication administration. Various modes of administration are provided by the system embodiments disclosed herein including parenterally administered medications, inhaler-based medications, among other modes of administration. Embodiments of the system described in greater detail below include applications for home use, in-office use by health care provider (HCP) or by the patient, hospital use, and educational use for training medical professionals and other personnel among other potential uses. The inventors have discovered a system for training individuals to use medical devices while improving user comfort and confidence in delivery and administration of medicament.

In addition to increasing confidence in self-administration in users by practicing with a medicament system, the inventors have identified additional benefits associated with multi-sensory learning regarding a medicament system. It has been discovered that multi-sensory learning establishes multiple pathways in separate areas in the brain and ultimately results in a highly effective learning experience. However, in order to gain benefits from multi-sensory learning devices, certain requirements must be met including but not limited to the following: the sources of stimuli must be in close proximity to one another; the sources of stimuli must be synchronous; the stimuli must be congruous semantically, otherwise the superior colliculus (area of the brain located in the midbrain known for integrating multiple sources of information) will segregate the stimuli instead of integrate them; and finally, the use of extraneous materials must be limited. With knowledge of the essential factors in multi-sensory learning and incorporation of the multi-sensory learning features into a training system, the inventors have developed a novel, cutting-edge medicament system.

Exemplary embodiments of the medicament delivery training device can be implemented to educate users on the proper operation and usage of a medicament device. The medicament system can be used to make prospective and current users of medicament devices feel more comfortable and confident in self-administration (or administration to others) of medicaments, and can help users understand the proper steps of medicament delivery. Exemplary embodiments of the medicament system can be used by a user before the user administers a medication by way of, for example, an auto-injector by way of using an actual automatic injection device corresponding to the automatic injection training device and/or can be used as needed or desired by the user. Other exemplary embodiments of the invention herein pertain to manual injection devices and manual injection training devices used by the user, respiratory inhaler trainers and respiratory inhaler drug delivery devices, in non-limiting examples.

The medicament system takes advantage of the multisensory learning capabilities of the human brain. As such, the medicament system provides the means to stimulate primarily the visual, auditory and somatic systems of the human nervous system.

Visual stimuli or feedback (visual output) can be generated mechanically or electronically. An example of a mechanically generated visual stimulus is a plunger moving past an inspection window in an autoinjector or prefilled syringe medicament device or a shroud extending from an injection device. An example of an electronically generated visual stimulus is one or more LED's blinking, an LCD display showing an icon, or key steps in the process of administration being highlighted on a screen in the order required for proper administration of medicament, in non-limiting examples. A visual output as disclosed herein includes but is not limited to a light, a display, a colorometric display system, a change in position of the device or any other type of visual cue to the user of the container and/or device. The visual output is associated with the medicament device or with the medicament training container; therefore it may be disposed on either portion of the system or provided in connection with the system either by a wire or wirelessly.

Additional visual outputs that may be incorporated into the system herein may include display devices having one or more layers of material having a light transmission region, a unit of information to be highlighted, and a light blocking region; and a backlight unit having a flexible, planar waveguide body, a light source configured to direct light into the waveguide body, and at least one light director associated with a portion of the waveguide body so as to direct light transversely to a plane of the waveguide body. The directed light travels through the light transmission region, and the directed light is directed toward the unit of information to be highlighted as provided in International Application No. PCT/US11/26976 and U.S. National Stage application Ser. No. 13/582,560 which claim the benefit of U.S. Provisional Application Ser. No. 61/310,081, which are incorporated by reference in their entireties herein. The unit or units of information to be highlighted may include the stepwise instructions for administering the medicament to a user and may also provide the duration of each step by way of highlighting each step for a predetermined amount of time such that the user can follow the precise timing of each step in the sequence.

Auditory stimuli or feedback (audio output) can also be generated mechanically or electronically. An example of a mechanically generated auditory stimulus is the "click" that can be heard if two parts of a device interlock. An example of an electronically generated auditory stimulus is a beeper or a speaker that plays spoken instructions. An audio output as disclosed herein can be generated mechanically or electronically, for example, and includes but is not limited to music, a sound, a beep, a series of beeps music or sounds, a mechanical sound including clicking, the movement of one or more parts of a medicament device relative to one another, or a sound replication of operation or behavior of a drug delivery device containing medicament. These auditory stimuli, such as two parts of a device interlocking can be picked up by a microphone of the system. The microphone may be associated with the collateral device in a non-limiting example, and may receive audio input from the medicament device as described above during use of the system. The system can then identify whether or not the device was used correctly (i.e., whether a step was performed correctly or in the correct order, for example). A combination of both visual and auditory output may include a video tutorial providing instructions to a user on proper administration of the medicament or use of the training device, for example.

Somatic stimuli or feedback, also called somatosensory stimuli or tactile feedback, is typically generated mechanically. In a typical embodiment of the medicament system, there are a large number of somatic stimuli, particularly with reference to the medicament device, such as actuation forces, abrasion resistance, frictional forces, spring compression, the feel of a click if two parts interlocking, surface texture, vibrations, weight sensation, and any other similar stimuli or feedback known to those of skill in the art.

A "predetermined value" as used herein, for example, includes but is not limited to a value or range of values relating to an event involving use or operation of the device. These may include, but are not limited to thresholds, ceilings, baselines or range values that are desired or undesired for a particular event. Examples of predetermined values include, but are not limited to, a predetermined orientation value, predetermined time value, or a predetermined contact value, in addition to other predetermined values described herein refers to a value that is used as a reference value in relation to a value, signal, or indication that is detected by, for example, a sensor of the medicament device. Predetermined value may include an optimal value, or a sub-optimal value, or any value there between, or any combination thereof. The term "value" as used herein, may refer to a specific value or a range of values.

In one example, a predetermined perpendicularity value may include a 90 degree angle between the device and a target region for the medicament device, an additional predetermined perpendicularity value may include a 10 degree angle between the device and a target region for the device. At either predetermined perpendicularity value, or at any value there between, a signal output component may be initiated. The signal output component may therefore be an error message or a congratulatory message, for example. This signal output component may be initiated from the medicament device and/or the medicament training container.

The term "condition" as used herein includes but is not limited to one or a combination of a user input, a status of the medicament device or the medicament training container, anything that is sensed by the device or container, correct or incorrect stepwise activities, usage of the device over time, among other conditions.

The term "error condition" as used herein includes but is not limited to one or a combination of a condition pertaining to a mistake by the user in using the device, whether the mistake is incorrect positioning or contact between the device and the user, or whether the mistake is an out of order step, a step that exceeds or fails to meet predetermined time value (such as an undue pause during or between steps, or insufficient time for conducting a step or transition between steps). Error conditions may also include errors of the device itself or of the container, including low or lack of power or failure to operate as intended.

The term reconstituted as used herein includes a return of the components to their original state. For example, following use of the medicament device, once the device is in a post-delivery state (or post training state), it can be reset for subsequent use. As part of the resetting of the device from a post-delivery (or post-training) state to a pre-delivery (or pre-training) state, the signal output components including audio, visual, olfactory, gustatory, and tactile are also reset back to their original states, or reconstituted, such that a subsequent training or medicament delivery can be performed with the device. The term reconstituted may also include return of the medicament training container to its original state and may include a return of the stepwise instructions to the first step in the sequence or a replacement of the medicament device within the medicament training container in preparation for a subsequent medicament delivery or training, for example.

The term "fluid" as used herein may include any type of fluid, including but not limited to liquid or gas. The fluid may specifically include a liquid, powder or aerosol medicament, air flowing to or from the user, or liquid coming from the user, in some non-limiting embodiments.

The terminology used herein is for the purpose of describing particular embodiments only and is not intended to be limiting. As used herein, the singular forms "a," "an," and "the" are intended to include the plural forms as well, unless the context clearly indicates otherwise these terms do not denote a limitation of quantity, but rather denote the presence of at least one of the referenced item. For example "a sensor" may denote the presence of at least one sensor; however, multiple sensors may be contemplated unless otherwise specifically stated. Furthermore, to the extent that the terms "including," "includes," "having," "has," "with," or variants thereof are used in either the detailed description and/or the claims, such terms are intended to be inclusive in a manner similar to the term "comprising." Moreover, unless specifically stated, any use of the terms first, second, etc., does not denote any order, quantity or importance, but rather the terms first, second, etc., are used to distinguish one element from another.

The term "sensor" or "sensors" as used herein may include but are not limited to, light sensors, fluid flow rate sensors, strain gauge sensors, temperature sensors, pressure sensors, tilt sensors, force sensors, level sensors, contact sensors, photoelectric sensors, magnetic sensors, ultrasonic sensors, electrochemical sensors, acceleration sensors, moisture sensors, humidity sensors, speed sensors, inductive sensors, capacitive sensors, and orientation sensors. Some of these sensors may require a supply of voltage. The medicament system may include one or more of the sensors described herein, for example, a contact sensor may be used to detect removal or placement of the smart device onto the medicament device, for example, or removal or placement of the medicament device onto the user, in another example. In a further example, two or more contact sensors, more preferably the contact sensors may be used to detect perpendicularity of the medicament device relative to a target area of a patient. An example of an inductive sensor includes material embedded in or associated with the medicament device, wherein said embedded or associated material proportionally changes the magnetic field of the inductive sensor which may be associated with or embedded in the smart device, in one non-limiting example, depending on its distance away from the inductive sensor. The sensor then outputs a variable electrical signal based on the distance between the embedded or associated material and the inductive sensor.

The tactile or vibration component may include a vibration system, which provides a vibratory sensation. In one embodiment, this vibrator system may include a motor, in a non-limiting example a small DC motor, a gear and a weight. The weight may be mounted off-center on the gear, such that when the motor spins, the gear/weight combination at 100 to 150 rpm for example, the off-center mounting creates a vibration. In another embodiment, a linear transducer may be used. In a further example, an eccentric motor can be used to provide an oscillation or vibration.

The terms "medicament training system" and "medicament system" may be used interchangeably herein. The medicament training system or medicament system may be used to train a user to use a medicament delivery device during, before, or after use of the medicament delivery device. A "medicament delivery device" refers to a medicament device that may be used to deliver medication to a user.

The term "medicament device" as used herein may include a training device or a medicament delivery device (i.e., drug delivery device), or a combination thereof. In one non-limiting embodiment, a medicament device may be used to both train a user to use the medicament device and also deliver medicament to the user. In a particular non-limiting embodiment, a medicament device may include different modes, wherein one mode may be used for training only, another may be used for medicament delivery only, and a further mode may be used for training or guidance during medicament delivery, for example. The medicament device may include medicament in some non-limiting embodiments. In other non-limiting embodiments, the medicament device may not include medicament. The medicament device may include an injection device such as an auto-injector and/or trainer, an inhaler device and/or respiratory trainer, a bolus injector, a nasal inhaler device, a needless injector, a transdermal patch, an ampoule, a medicine container, a medicine package, a vial, a metered-dose inhaler, a dry powder inhaler, a prefilled syringe, among other medicament devices known to one of ordinary skill in the art. In non-limiting embodiments, the medicament device may include a housing, and the housing may include a mechanism having one or more mechanical components associated with the housing that move relative to one another to produce a visual, a tactile and/or an audible output detectable by a detecting component of the collateral device, for example.

The term "associated" or "association," as used herein, includes but is not limited to direct and indirect attachment, adjacent to, in contact with, partially or fully attached to, and/or in close proximity therewith. The term "in conjunction with" as used herein includes but is not limited to synchronously or near synchronous timing, the phrase may also include the timing of outputs, where one output directly follows another output.

Any of the abovementioned outputs by the signal output component can be presented along with or in conjunction with any of the other outputs of the device. For example, a visual and an audio stimulation or feedback may occur at the same time or within the same step of the training to enhance training of the user. Furthermore, the inventors have discovered that a combination of mechanical feedback (kinesthetic) and electronic feedback enhances the learning experience of a user when using the medicament training system.

Embodiments of the medicament system herein may be provided wherein various components of the system may be incorporated into either one of a medicament device or a collateral device, or both. Some components of the system may be in the medicament device and other components of the system may be in the collateral device, in a non-limiting embodiment.

In one embodiment, a medicament system configured to communicate information about a medicament device or about a use of a medicament device, or a combination thereof, to a user, is provided. The medicament system may include a medicament device including a housing, and a collateral device, wherein the collateral device may include an information detecting and/or receiving component configured to receive information from the medicament device and/or a sending component configured to send information to the medicament device, and optionally at least one of: a) a signal output component; b) a microprocessor; c) a storage medium component; and d) a power source, and wherein the medicament device may be configured to generate information detectable by the collateral device, or transmit information to the collateral device, wherein the collateral device may be configured to detect and/or receive information about the medicament device from the medicament device and provide information about the medicament device and/or a feedback about a use of the medicament device to a user of the system. The medicament device may further include a transmitter configured to communicate information and/or signals from the medicament device to the collateral device and/or a remote device, and/or receive information and/or signals from a collateral device and/or a remote device.

In a further embodiment, the collateral device of the system may be able to receive or obtain information from a remote source as well as send information to a remote source such as the Internet, a database, a telephone, a computer, or other source, in non-limiting embodiments. The information and/or signal sent or received may include information about the medicament device, a user, a medicament, a use of the medicament device, instructions for using the medicament device or the medicament, a physician or other healthcare provider, a hospital, a pharmacy, in non-limiting examples. In a non-limiting embodiment, the collateral device may include a Smartphone which will be described in more detail below.

The signal output component may be configured to output an audio, a visual, a tactile, a gustatory, or an olfactory signal, or a combination thereof, to the user, in non-limiting embodiments.

In another embodiment, the collateral device includes the power source. In another embodiment, the information detecting component may detect movement of the medicament device or components thereof. In some embodiments, the medicament device may include one or more mechanical parts or components that may move relative to one another. The detecting component may detect movement of the medicament device and/or movement of the mechanical components of the medicament device by visual detection in non-limiting embodiments. In addition, or in an alternative embodiment, the detecting component may, detect audio caused by movement of the one or more mechanical parts or components, or movement of components of the medicament device relative to one another by audio detection. The information detected may be provided to a microprocessor and a signal may be provided to a user. Furthermore, the information detected may be stored on the storage medium component. In one non-limiting embodiment, the detecting component may include a camera and/or a motion sensor. In another non-limiting embodiment, the detecting component may include a microphone. In a further, non-limiting embodiment, the detecting component may include both an audio and a visual detection component.

In another embodiment, the receiving component may be configured to receive a signal from the medicament device. The signal may provide information about the medicament device, a medicament associated with the device and/or a use of the medicament device. In a non-limiting embodiment, the receiving component includes a microphone, and the signal received from the medicament device is an audible signal, wherein the microphone is configured to receive the audible signal from the medicament device and/or a mechanical sound produced by a mechanism including one or more mechanical components associated with the housing of the medicament device during use of the medicament device.

In a further embodiment, the medicament device may communicatingly connect to the collateral device via a wired or a wireless connection, wherein said connection provides a communication of power and/or information between the medicament device and the collateral device. In some non-limiting embodiments, communication between the medicament device and the collateral device includes one way communication of power and/or information from the collateral device to the medicament device, or from the medicament device to the collateral device, and two-way communication of power and/or information to and from the medicament and collateral devices.

In one non-limiting embodiment, the medicament system is provided wherein the wireless connection includes a Bluetooth® and/or an RFID (Radio Frequency Identification) technology. In a further embodiment, the RFID technology includes an RFID transponder and an RFID reader. In another non-limiting embodiment, the RFID transponder is associated with the collateral device and the RFID reader is associated with the medicament device, the medicament device includes the power source, such that the RFID reader of the medicament device can power the collateral device by way of the RFID transponder.

The RFID transponders, or tags, described herein may be active, semi-active or passive and may include a microchip and an antenna. The active and semi-active RFID transponders may additionally include a battery, in a non-limiting example.

In another non-limiting embodiment, the RFID transponder is associated with the medicament device and the RFID reader is associated with the collateral device wherein the collateral device includes the power source, and wherein the RFID reader of the collateral device powers the medicament device by way of the RFID transponder.

In a further embodiment, the medicament system is provided wherein one of the medicament device or the collateral device comprises a unique identification component. The unique identification component may include, in non-limiting embodiments, information about a medicament, the medicament device, use of the medicament device, or information about the collateral device, or other information know to one of ordinary skill in the art. The other of the medicament device or the collateral device may include a unique identification reader, wherein the unique identification reader is configured to read information on or associated with the unique identification component, in an embodiment. In one non-limiting embodiment, the unique identification component may include a bar code and the unique identification reader may include a bar code reader.

In another embodiment, the medicament system is provided wherein the collateral device includes or is configured to receive pre-programmed information. The pre-programmed information may include information about a medicament device, in a non-limiting embodiment. The pre-programmed information may include information about a medicament, a user, a healthcare provider, a healthcare facility, or other information, in other non-limiting embodiments.

In a further embodiment, the medicament system is provided wherein the collateral device is configured to download or receive information from a database, the Internet, and/or another device. The information may include information about a medicament, a medicament device including instructions for use, contraindication of medicaments, information about a user, medicament dosage information, storage information, prescribing physician information, pharmacy information, manufacturer information, warning information, recall information, in non-limiting embodiments, environmental data, geographical information, time zone information, MET (meteorological) data, storage information, supply chain information, transit data, and/or temperature data.

In a non-limiting embodiment, the collateral device may include the signal output component, the microprocessor, the storage medium component and the power source. In another embodiment, the signal output component may include a speaker, a display, a light, a vibration component, a smell-emitting component, or a temperature-changing component, or a combination thereof.

In a further embodiment, the medicament system is provided wherein the collateral device may be configured to detect a condition of the medicament device in response to information received by the information detecting and/or receiving component and/or information received via the wired or wireless connection with the medicament device. In a further embodiment, the condition may include an error condition, a correct usage of the system, and/or an input sensed by the system. In another embodiment, the medicament system may provide a feedback to a user of the system via the signal output component. This feedback may be based on a condition detected, in a non-limiting embodiment.

In another embodiment, the medicament system may provide instructions for using the medicament device in a sequence of steps, wherein the microprocessor is configured to control a provision of the instructions for using the medicament device to the user in the sequence of steps and/or to provide an instruction to the user based on information detected and/or received by the information detecting and/or receiving component of the collateral device.

In a further embodiment, the system may include a sensor associated with the medicament device, wherein the sensor may be configured to detect a condition of the medicament device. Information about the condition detected by the sensor may be communicated to the collateral device and/or to a user from the medicament device, in an embodiment. The information that is communicated to the collateral device may further be provided from the collateral device to the user in a non-limiting embodiment.

In another non-limiting embodiment, a medicament system configured to communicate information about a medicament device or about a use of a medicament device, or a combination thereof, to a user is provided. The medicament system includes a medicament device including a housing, the medicament device including a sensor associated therewith, a transmitter configured to send information from the medicament device, and optionally at least one of: a) a signal output component; b) a microprocessor; c) a storage medium component; and d) a power source, the medicament system including a collateral device, the collateral device including an information detecting and/or receiving component configured to receive information produced from the sensor and/or a sending component configured to send information to the medicament device, a signal output component, a microprocessor, a storage medium component, and a power source, wherein the collateral device is configured to detect and/or receive information about the medicament device from the medicament device, and/or send information to the medicament device, and/or to provide information about the medicament device and/or a feedback about a use of the medicament device to a user of the system.

In another embodiment, the medicament system is provided wherein the collateral device includes the microprocessor, the storage medium component, the power source, and the signal output component. In a further embodiment of the medicament system, the medicament device may communicatingly connect to the collateral device via a wired and/or a wireless connection, wherein said connection provides a communication of power and/or information between the medicament device and the collateral device. A communication of power or information can be either one way or two-way. One way communication may occur from the collateral device to the medicament device or vice versa, and two-way communication between the collateral device and the medicament device may occur, in non-limiting embodiments. Communication of power may be from the collateral device to the medicament device in one non-limiting embodiment, from the medicament device to collateral device in another non-limiting embodiment. As aforementioned, the communication may be one way communication or two way communication between the components of the system. In one particular non-limiting embodiment, information communication is communicated from the medicament device to the collateral device, and power may be communicated from the collateral device to the medicament device.

In a further embodiment, the medicament system is provided wherein the wireless connection includes a Bluetooth® and/or an RFID technology. In a further embodiment, the RFID technology comprises an RFID transponder and an RFID reader. In still a further embodiment, the RFID transponder is associated with the collateral device and the RFID reader is associated with the medicament device, the medicament device including the power source, such that the RFID reader of the medicament device can power the collateral device by way of the RFID transponder.

In an alternative embodiment, the RFID transponder may be associated with the medicament device and the RFID reader may be associated with the collateral device, wherein the collateral device includes the power source, and wherein the RFID reader of the collateral device powers the medicament device by way of the RFID transponder.

In a further embodiment, the medicament system is provided wherein one of the medicament device or the collateral device includes a unique identification component, the unique identification component including information. In non-limiting embodiments, the information may include information about a medicament, the medicament device, use of the medicament device, or information about the collateral device. In a non-limiting embodiment, the other of the medicament device or the collateral device includes a unique identification reader, said unique identification reader being configured to read information on the unique identification component.

In a further embodiment, the unique identification component includes a bar code and the unique identification reader includes a bar code reader. In a further embodiment, the medicament system may be provided wherein the collateral device includes pre-programmed information. The pre-programmed information may include information about one or more medicament devices, about one or more medicaments, about one or more users, or other information know to one skilled in the art.

In a further embodiment, the medicament system may be provided wherein the collateral device is configured to download or receive information from a database, the Internet, and/or another device, the information may include information about one or more medicaments, one or more medicament devices including instructions for use, contraindication of medicaments, information about one or more users, medicament dosage information, storage information, prescribing physician information, pharmacy information, manufacturer information, warning information, recall information, environmental data, geographical information, time zone information, MET (meteorological) data, storage information, supply chain information, transit data, and/or temperature data, in non-limiting embodiments.

As aforementioned, the signal output component of the medicament system may include a speaker, a display, a light, a vibration component, a smell-emitting component, or a temperature-changing component, or a combination thereof in non limiting embodiments. In another embodiment of the medicament system, the medicament device may include a mechanism including one or more mechanical components associated with the housing that move relative to one another to produce a visual, a tactile and/or an audible output detectable by the detecting component. In a further embodiment of the system, the collateral device may be configured to detect a condition of the medicament device in response to information received by the information detecting and/or receiving component and/or information received via the wired and/or wireless connection with the medicament device.

In a further embodiment the medicament system is provided wherein the condition includes an error condition, a correct usage of the system, and/or an input sensed by the system. In still a further embodiment, the system may provide a feedback to a user of the system via the signal output component based on the condition detected. In another embodiment, the system may provide instructions for using the medicament device in a sequence of steps, and the microprocessor may be configured to control a provision of the instructions for using the medicament device to the user in the sequence of steps and/or to provide an instruction to the user based on information produced from the sensor of the medicament device.

In yet another embodiment, a medicament system configured to communicate information about a medicament device or about a use of a medicament device, or a combination thereof, to a user, is provided. The medicament system includes a medicament device having a housing, a collateral device comprising a sensor, and an attachment component configured to secure the collateral device to the medicament device. The system may further include in an embodiment, a sending component configured to send information to the medicament device and/or the collateral device, an information detecting and/or receiving component configured to receive information from the medicament device about the medicament device and/or about a use of the medicament device. In embodiments of the system in which the collateral device is attached or secured to the medicament device, the collateral device may not require an information detecting and/or receiving component configured to receive information from the medicament device as the collateral device will sense the condition of the medicament device by virtue of the attachment in non-limiting embodiments. The system may further include a signal output component, a microprocessor, a storage medium component, and a power source, wherein the signal output component is configured to provide an output comprising information about the medicament system and/or information about a usage of the medicament device or system to a user of the system.

In a further embodiment the medicament system is provided wherein the medicament device includes the microprocessor, the storage medium component, the signal output component, and the power source. In still a further embodiment, the medicament device may communicatingly connect to the collateral device via a wired and/or a wireless connection, wherein said connection provides a communication or transmission of power and/or information between the medicament device and the collateral device. In one non-limiting embodiment, the wireless connection may be short-range wireless connection, such as Bluetooth® connection in one non-limiting example. In a non-limiting embodiment, where a Bluetooth® connection is used a power source may be provided in both the medicament device and the collateral device. The power source may include a battery, in one non-limiting example.

In a further embodiment, the wireless connection may include a Bluetooth® and/or an RFID technology. The RFID technology may include an RFID transponder and an RFID reader as described above, and the locations of and associations between the RFID transponder and reader may be provided as described above in regard to the other embodiments disclosed herein.

Furthermore, the medicament system embodiment may further include a unique identification component and unique identification reader wherein one of the medicament device or the collateral device includes a unique identification component, the unique identification component including information about a medicament, the medicament device, use of the medicament device, or information about the collateral device, in non-limiting embodiments. The other of the medicament device or the collateral device may include a unique identification reader, said unique identification reader being configured to read information on or associated with the unique identification component. In a further non-limiting embodiment, the unique identification component is a bar code and the unique identification reader is a bar code reader.

In a non-limiting embodiment of the medicament system, the collateral device may include the microprocessor and the storage module, the collateral device including pre-programmed information about one or more medicament devices and/or instructions for use for one or more medicament device and/or medicaments associated therewith, for example. In a further embodiment, the collateral device may be configured to download or receive information from a database, the Internet, and/or another device, the information may include information about one or more medicaments, one or more medicament devices including instructions for use, contraindication of medicaments, information about one or more users, medicament dosage information, storage information, prescribing physician information, pharmacy information, manufacturer information, warning information, recall information in non-limiting embodiments, environmental data, geographical information, time zone information, MET (meteorological) data, storage information, supply chain information, transit data, and/or temperature data. Such temperature data may include, in embodiments in which the medicament device includes medicament, what temperature the medicament has been kept at and/or a report of temperatures that the medicament device and/or medicament has been subjected to from the manufacturer to the user, for example. Other temperature data may include temperature data indicating required or suggested storage temperatures for medicaments and/or medicament devices.

In still a further embodiment, the signal output component of the medicament system may include a speaker, a display, a light, a vibration component, a smell-emitting component, or a temperature-changing component, or a combination thereof.

In another embodiment of the medicament system, the medicament device may include a mechanism including one or more mechanical components associated with the housing that move relative to one another to produce a visual, a tactile and/or an audible output detectable by the detecting component. In one non-limiting example, wherein the medicament device includes a respiratory device or trainer and specifically a metered dose inhaler, for example, the one or more mechanical components of the medicament device may include the components of the metered dose inhaler housing that move relative to one another when the inhaler is actuated.

In a further embodiment of the medicament system, the collateral device may be configured to detect a condition of the medicament device in response to information received by the information detecting and/or receiving component and/or information received via the wired and/or wireless connection with the medicament device, and/or information sensed by the one or more sensors. In one non-limiting example, the collateral device may detect movement of the components of the medicament device by way of a camera, for example, such as detecting the movement of the mechanical components of a metered dose inhaler device when the metered dose inhaler device is actuated, for example. In another non-limiting example, the collateral device may detect movement of or a condition of the medicament device by way of a microphone which listens for sounds generated by the movement(s) of the medicament device and/or its components to indicate, for example, the cap has been removed, a safety shield has been depressed in preparation for an injection with an injection device, in non-limiting embodiments.

In a further embodiment, the condition detected may include an error condition, a correct usage of the system, and/or an input sensed by the system. In still a further embodiment, the system may provide a feedback to a user of the system via the signal output component. In some embodiments, this feedback may be based on the condition detected.

In still a further embodiment, the system may provide instructions for using the medicament device in a sequence of steps, wherein the microprocessor is configured to control a provision of the instructions for using the medicament device to the user in the sequence of steps and/or to provide an instruction to the user based on information received from the sensor of the medicament device.

In a further embodiment, the attachment component may include a hook, a clip, an adhesive, a holder which may be contoured to receive the medicament device in a non-limiting embodiment, a magnet, or a combination thereof, or any other type of attachment component known to one of ordinary skill in the art. In one non-limiting embodiment, an attachment component may be formed by a portion of the housing of the collateral device, the attachment component may include a surface of the housing, wherein the surface is complementary in shape to the portion of the medicament device upon which it is to be attached, therefore, in one non-limiting example, the attachment component may be snapped onto the medicament device by contact with the surface of the housing of the medicament device and the complementary surface of the housing of the collateral device. In a non-limiting embodiment, the attachment component may be attached to one of the medicament device or the collateral device, and configured to attach the medicament device or the collateral device to the other of the medicament device or the collateral device. For example, the attachment component may be affixed to the collateral device and configure to attach the collateral device to the medicament device, in another non-limiting example, the attachment component may be affixed to the medicament device, and be configured to attach the medicament device to the collateral device. In a further non-limiting example, the attachment component may be a component separate from the medicament device and the collateral device, but may be configure to attach to both of the medicament device and the collateral device.

In the embodiments provided herein, the medicament system embodiments may further comprise a control interface, wherein the control interface may include a responsive member reactive to user input. The control interface may be associated with the medicament device and/or the collateral device in non-limiting embodiments.

Furthermore, as aforementioned herein, the medicament device embodiments described herein may include a medicament training device, a medicament delivery device, or a combination thereof.

In another embodiment, a collateral device configured to receive information from and/or detect information about a medicament device is provided. The collateral device includes a collateral device housing, and may further include a detecting and/or a receiving component, wherein the detecting and/or receiving component is configured to detect information about or receive information from the medicament device, a signal output component may be included, and configured to provide an output to a user, a power source, a microprocessor, and a storage module may be provided, wherein the collateral device may provide a feedback to a user based on information detected and/or received by the detecting and/or receiving component, in a non-limiting embodiment.

In a further embodiment, the collateral device may include a sensor. The sensor may be associated with the collateral device housing, in one embodiment. The sensor may include a proximity sensor, a perpendicularity sensor, a contact sensor, a temperature sensor, a motion sensor, a light sensor, a fluid flow rate sensor, a strain gauge sensor, a pressure sensor, a tilt sensor, a force sensor, a level sensor, a photoelectric sensor, a magnetic sensor, an ultrasonic sensor, an electrochemical sensor, an acceleration sensor, a moisture sensor, a humidity sensor, a speed sensor, an inductive sensor, a capacitive sensor, or an orientation sensor, or a combination thereof, in a non-limiting embodiment.

In one, non-limiting embodiment, the collateral device may include a housing having a top portion, a bottom portion, and an opening for receiving the medicament device. In this particular embodiment, the collateral device may include a first sensor configured to protrude into the opening, wherein a contact between the medicament device and the first sensor indicates that a cap of the medicament device has been removed before placement into the collateral device, as a result of the shape of the distal end of the housing of the medicament device with the cap removed, and the resulting contact between this portion of the medicament device and the first sensor. Therefore, insertion of the medicament device into the collateral device causes information to be detected via the first sensor that the cap has been removed from the medicament device prior to insertion, resulting in activation of the first sensor as the first sensor contacts the medicament device. Further insertion of the medicament device into the collateral device causes the first sensor to move from a first position to a second position, further activating the first sensor as it is moved from the first to the second position as the medicament device is further inserted into the collateral device. In a non-limiting embodiment, the first sensor may include a mechanical switch, or contact switch.

A second sensor may be provided in near, or adjacent to the opening of the collateral device, wherein the second sensor is configured to detect a position of a needle shield of the medicament device. Further insertion of the medicament device into the collateral device causes the needle shield to contact the bottom portion of the collateral device, movement of the medicament device against the bottom portion of the collateral device causes retraction of the needle shield enabling actuation of the medicament device. The second sensor, in a non-limiting embodiment, may contact the medicament device when the needle shield is in a retracted position. This may be due to the placement of the second sensor as well as the tapered shape of the distal end of the medicament device housing, such that the medicament device housing only contacts the second sensor when the needle shield has been fully retracted. The second sensor may include a contact sensor or a contact switch in non-limiting embodiments. Therefore, activation of the first and second sensors may indicate that the medicament device is activated and ready for use. Feedback may be provided to a user via the medicament device or the collateral device during the interaction between the medicament device and the collateral device before and after the medicament device is activated for use. In one non-limiting embodiment, the collateral device may include an aperture in the bottom portion to allow an injection member to traverse the bottom portion of the collateral device during use of the device. In another embodiment, no aperture is provided.

The collateral device may further include a third sensor on a bottom surface of the collateral device. In another, non limiting embodiment, the third sensor may form a portion of the bottom of the collateral device. In one embodiment, this third sensor may include a capacitive sensor, for example. The third sensor may sense when the collateral device is against the skin of a user. The third sensor may additionally sense when a contact between the safety shield and the third sensor has been made. Consequently, either alone, or in combination with the second sensor, the third sensor may indicate to a user that the medicament device has been fully inserted into the collateral device, the collateral device is against the skin of the user and ready for use, and the safety shield has been retracted into the housing of the medicament device. A combination between contact of the second sensor with the medicament device distal end and contact of the third sensor with the medicament device would indicate the shield has been fully depressed (i.e., retracted), and the injection device is ready for activation.

In a further embodiment, the collateral device may include an internal element that is movable relative to the collateral device. The internal element may include one or more sensors, and may include an opening configured to receive a portion of the medicament device. The internal element may be disposed within the opening of the collateral device, and may receive the medicament device, and be displaced upon movement of the medicament device relative to the collateral device. The collateral device may be placed against the skin of the user, the medicament device distal end may be placed within the opening of the internal element, a spring may be provided to allow displacement and replacement of the internal element relative to the collateral device. Movement of the medicament device into the internal element opening causes activation of contact sensors to indicate removal of the cap of the medicament device and correct placement within the opening, additional sensors may sense contact between the collateral device or the internal element with the skin and with the distal end of the medicament device or the safety shield of the medicament device. These sensors may be provided, as described herein, to detect contact with the medicament device, and depression of the safety shield in preparation for use of the medicament device. Upon movement of the medicament device relative to the collateral device, the internal element is displaced from the collateral device into the skin of the user, the safety shield of the medicament device is depressed, and the medicament device may be actuated. The internal element may include an opening to allow for passage of the injection member of the medicament device to enter a target area on the user skin to deliver an injection. Following the injection, and release of any pressure on the medicament device, the biasing member may extend to retract the internal element into the collateral housing.

In other embodiments described herein, the collateral device may include an attachment component, which may be inherent in the shape and size of a portion of the collateral device, such that it mates with a complementary shape and size of the medicament device, so as to attach onto the medicament device in one, non-limiting embodiment. In other non-limiting embodiments, the attachment component may include an adhesive, a clip, or any other type of attachment component described herein or known to those skilled in the art to attach the collateral device onto the medicament device. In one embodiment, the collateral device may include a contact element and contact switch, wherein upon movement of the contact element relative to the collateral device, the contact element makes contact with the contact switch to register a status of the medicament device, such as, for example, depression of the safety shield of the device in preparation for an injection. Due to the position of the contact element when the collateral device is attached onto the medicament device, in this non-limiting embodiment, the interaction between the contact element and the contact switch registers that the shield has been deflected when the contact element presses against the contact switch, for example.

In a further embodiment, the collateral device is provided wherein the storage module includes pre-programmed information. The pre-programmed information may include information about a medicament device and/or instructions for use for a medicament device and/or a medicament associated therewith, in a non-limiting example. The collateral device may be further configured to receive or download information about a medicament, a medicament device, and/or a user from the Internet, from another device, and/or from a database, wherein the information can be received or downloaded via a wired and/or a wireless connection.

In still a further embodiment, the collateral device may be configured to provide instructions and/or a feedback to the user via the signal output component. In another embodiment, the collateral device may be configured to communicatingly connect to the medicament device via a wired and/or a wireless connection to provide communication or transmission of power and/or communication of information between the collateral device and the medicament device.

A communication of power or information can be either one way or two-way. One way communication may occur from the collateral device to the medicament device or vice versa, and two-way communication between the collateral device and the medicament device may occur, in non-limiting embodiments. Communication (or transmission) of power may be from the collateral device to the medicament device in one non-limiting embodiment, from the medicament device to collateral device in another non-limiting embodiment. As aforementioned, the communication may be one way communication or two way communication between the components of the system. In one particular non-limiting embodiment, information communication is communicated from the medicament device to the collateral device, and power may be communicated from the collateral device to the medicament device.

As described herein, the wireless connection may include a Bluetooth® or an RFID connection. The collateral device may further include a unique identification reader, in non-limiting embodiments, the unique identification reader may be configured to read information on a unique identification component associated with a medicament device or a medicament container, for example. The unique identification reader may include a bar code reader and the unique identification component may include a bar code in non-limiting embodiments.

In a further embodiment, the collateral device may be configured to communicate with, a medicament delivery device, a medicament training device, or a combination thereof. The collateral device may communicate with the medicament device(s) by receiving and/or sending information, receiving and/or sending signal(s), receiving and/or sending power, etc., in non-limiting examples.

In a further embodiment, the signal output component of the collateral device may include a speaker, a display, a light, a vibration component, a smell-emitting component, or a temperature-changing component, or a combination thereof as aforementioned herein.

In an embodiment, the collateral device may associate with a medicament device that includes a mechanism including one or more mechanical components associated with the housing of the medicament device, that move relative to one another to produce a visual, a tactile and/or an audible output detectable by the detecting component of the collateral device. The collateral device may be configured to detect a condition of the medicament device. This detection may be in response to information received by the information detecting and/or receiving component and/or information received via a wired and/or a wireless connection with the medicament device, in a non-limiting embodiment.

In a further non-limiting embodiment, the condition detected may include an error condition, a correct usage of the system, and/or an input sensed by the system. The collateral device may provide a feedback to a user of the system via the signal output component based on the condition of the medicament device detected, in a non-limiting embodiment. In a further embodiment, the collateral device may provide instructions for using the medicament device in a sequence of steps, and wherein the microprocessor is configured to control a provision of the instructions for using the medicament device to the user in the sequence of steps and/or to provide an instruction to the user based on information produced by or detected by the sensor of the medicament device. Error conditions may include, in non-limiting examples, putting cap back on a device, an out of sequence operation of a device, a wet injection, and not holding at 90 degrees when required.

In a further non-limiting embodiment, the collateral device may include an attachment component configured to attach the collateral device to the medicament device. In still a further embodiment, the attachment component may include a hook, a clip, an adhesive, a holder which may be contoured to receive a medicament device in a non-limiting embodiment, a magnet, or a combination thereof, in non-limiting examples. In another embodiment, the collateral device may include a control interface; the control interface may include a responsive member reactive to a user input. In still a further non-limiting embodiment, the information detecting and/or receiving component of the collateral device may include a camera and/or a microphone.

In another embodiment, a method of using a collateral device to train a user of a medicament device to properly operate the medicament device to dispense a dose of medicament and to provide an instruction and/or a feedback to a user of the collateral device is provided. The method may include detecting and/or receiving information from a medicament device, processing information received from the medicament device, and providing a signal output to a user based on information received and processed.

In a further embodiment, the method may include providing instruction and/or information related to a medicament device, a medicament, and/or a user to a user, wherein the instruction and/or information is stored on a storage module associated with the collateral device, in a non-limiting embodiment. The method may further include providing instruction and/or information related to a medicament device, a medicament, and/or a user to a user, wherein the instruction and/or information is received by the collateral device via a wired and/or a wireless connection, in a non-limiting embodiment.

In still a further embodiment, the method may include electronically reading information from a unique identification component associated with the medicament device and/or a medicament, wherein the information is output to a user.

In another embodiment, a collateral device configured to receive information from and/or detect information about a medicament device is provided. The collateral device includes a collateral device housing, a sensor associated with the housing; and an attachment component associated with the housing, wherein the attachment component is configured to attach the collateral device to the medicament device. In a further embodiment, the collateral device may include a signal output component configured to provide an output to a user, the output may include information about the medicament device, information about a use of the medicament device, information about a user of the collateral device, and/or information about a medicament, in non-limiting embodiments.

In the embodiments described herein, the collateral device may include a Smartphone, a computer, a PDA, or the like. These devices may include the microprocessor, information detecting component and receiving component, signal output component, storage medium, power source, or a combination thereof, such that a signal or information from a medicament device can be received by a Smartphone device, in a non-limiting example, and the Smartphone may provide the feedback or output to the user based on the information or signal received. A display of the Smartphone may be beneficial to provide feedback to a user based on information received from the medicament device or received from a remote source such as the Internet, a database, another phone, or a remote computer, in non-limiting examples. In these non-limiting embodiments, it is beneficial to take advantage of the components already existing in a Smartphone (or other similar device), to provide training or guidance to a user during use of the medicament device.

Embodiments of the system and medical device described herein may include sensors to provide users with an active learning experience. If an error is made in the training sequences, patients are notified through spoken instructions and taught how to overcome the error in non-limiting embodiments. If the user makes a mistake, in a non-limiting embodiment, the training injector may provide spoken guidance and encouragement to help establish synchronous motor skills to prevent errors in the future.

In another non-limiting embodiment, the wireless communication between the medicament device and the collateral device may include Radio Frequency Identification technology, for example. If the devices communicate by way of RFID, either device may include the power source, and the device without the power source can be powered by the device with the power source. In a non-limiting example, the collateral device may include a power source, and the medicament device may not include a power source. In this example, the collateral device may include an RFID reader and the medicament device may include an RFID transponder, wherein the RFID transponder may be powered by the RFID reader.

In a non-limiting embodiment, the collateral device may be preprogrammed to interact with various configurations of medicament devices. Medicament devices may include inhalation devices or inhalation training devices, injection devices including autoinjectors, pre-filled syringes or any other devices for parenteral administration of medicament (or related training thereof), devices including medicament bottles or tubes housing medicament (such as, for example, a pill bottle containing capsules or tablets or a vial containing medicament in non-limiting examples). The collateral device can be configured to associate with one or more medicament devices and one or more medicament training containers, in non-limiting embodiments. Information can be communicated between devices of the system by means known in the art, communication may occur between the medicament device and the collateral device and optionally between the medicament device and/or the collateral device and a remote device.

Information communicated between devices may include, for example, compliance information including information about the usage of the system or device. Additional information may include previous uses of the medicament device and/or system, correct and incorrect usage of the device and/or system as well as instructions for use of various medicament devices, contraindications related to various medicament devices and various medicaments, possible medicament interactions, safety information and storage information, reminders or timers identifying next scheduled administration of medicament, dosage information, volume and/or strength of medicament, other instructions regarding medicament including, but not limited to compliance to therapy or treatment, warnings, and any other instructions, among other information typically associated with medicaments and medicament devices. Information may further be communicated between the collateral device and a remote device, such as, for example, a Smartphone, a computer, a database, a PDA, a digital or analog watch, other remote device, or other information receiving device. Information communicated from the collateral device may include information about a use of the medicament device, in a non-limiting embodiment. The remote device may be adapted to receive the information and/or process the information and provide a feedback to a user of the system or an additional user such as a medical professional, a family member, or other person or entity. Information may be communicated between the collateral device and one or more remote devices, between the collateral device and the medicament device, or between the medicament system or medicament training device and one or more remote devices. Information can be communicated, as described herein, by way of wired and/or wireless communication. Feedback provided by the remote device may include training information, information about a correct or incorrect usage of the device, system, or medicament, error correction information, positive feedback, reminders regarding using the device, system, or taking a medicament. Other reminders may be provided by the remote device including, but not limited to reminders to make an appointment with a physician, reminders to refill a prescription, reminders to take a medicament, reminders to train using the medicament device, collateral device and/or system, among other reminders.

Non-limiting examples of collateral devices described herein may include a Smartphone, a non-electronic device, other types of electronic devices including, but not limited to, a computer, a PDA, a tablet, a digital or analog watch, for example.

In additional embodiments of the systems and devices provided herein, an intermediate collateral device may be provided, wherein the intermediate collateral device may associate with, or in a non-limiting embodiment, be attached to the medicament device. The intermediate collateral device may include a sensor and/or a transmitter in a non-limiting embodiment. The intermediate collateral device may be configured to communicate (i.e., communicatingly connects) either wirelessly or by wired connection with the medicament device, a collateral device, and/or a remote device. The communication may include one-way communication to or from the intermediate collateral device, or two-way communication there between. The communication may include a communication of power or information, including a communication of signals there between. In alternative non-limiting embodiments, the intermediate collateral device may be attached to a collateral device or a remote device.

Embodiments of the systems and devices disclosed herein may further include a remote communication component, wherein the remote communication component is configured to provide communication between the medicament system and/or the user and a remote source. The communication component may be used by a remote source (or entity) to contact the system and/or the user of the system or retrieve information therefrom or send information thereto. The communication component may also, or alternatively be used by the user of the system to access a remote source (or entity) to communicate therewith, receive information from and/or send information to. In non-limiting embodiments, the remote source may include emergency personnel or other healthcare professional, a pharmacy personnel, a help personnel or system operator who may be able to answer questions regarding the device or system or receive information there from, a computer or central network accessible for help using the system, for example, and/or a family member or other person, for example. The remote communication component may provide access to the user via the system to a remote source and/or provide remote source access to the system and/or the user.

Non-limiting embodiments of the system and device are provided in the Figures described herein. FIG. 1 provides a schematic view of a medicament system 100 comprising a medicament device 10a and a collateral device 12a. The medicament device 10a comprises a housing 14, which may include one or more mechanical components that may move relative to one another during the use of the medicament device 10a in non-limiting embodiments. For example, where the medicament device 10a includes a respiratory inhaler device or trainer, there may be one or more mechanical components of the device that when moved relative to one another during use of the device makes signature clicking sounds. These clicking sounds can be observed by a user and may be indicative as to whether the device is being used correctly or incorrectly. Any of the medicament device embodiments described herein may include one or more mechanical components.

The collateral device 12a of FIG. 1 further includes an information detecting component 16, an information sending and/or information receiving component 18 (the sending and receiving components may be two separate components in other non-limiting embodiments), a microprocessor 20, a storage medium component 22, a power source 24, and a signal output component 26. The information receiving component 18 and/or the information detecting component 16 of the collateral device 12a may be able to receive signals or information from and/or detect movement of the medicament device 10a, or components thereof. This information may be used to determine whether the medicament device is being used, whether it is being used correctly, and to provide any other information about the medicament device and/or from the medicament device 10a to the collateral device 12a. The information detecting component 16 may include a camera or a microphone, in non-limiting examples.

The information sending component of the collateral device 12a may be used to send information or signals to the medicament device 10a, in a non-limiting embodiment. The signal output component 26 of the collateral device 12a may be used to provide information and feedback to a user of the system 100, in a further embodiment. This feedback may be provided by any means known in the art, including but not limited to, by visual stimuli, audio, vibration, temperature change, gustatory and other types of feedback may also be used. Consequently, the signal output component may include a light or display, or a combination thereof, and/or a speaker, in non-limiting embodiments. The storage medium component 22 may be used to store information including instructions for using the medicament device 10a in an embodiment, and more specifically, stepwise instructions in a further embodiment. The storage medium component 22 may further include information about, instructions for use of multiple medicament devices among other information stored thereon. This information may be stored on the storage medium component 22 and may be pre-loaded and/or retrieved by the system 100 in non limiting embodiments.

In another embodiment, a medicament system 200 is shown in the schematic view of FIG. 2, including a medicament device 10b having a housing 14, a collateral device 12b communicatingly connected to the medicament device via wired or wireless connection (wireless RFID connection shown in FIG. 2). The wireless RFID (Radio Frequency Identification) connection is shown in FIG. 2, wherein the RFID transponder 30 is associated with the medicament device 10b, and the RFID reader 32 is associated with the collateral device, however, in other embodiments the RFID components may be associated with other devices of the system and/or the RFID transponder 30 may be associated with the collateral device 12b and the reader 32 associated with the medicament device 10b, in non-limiting examples. Information and signals may be communicated between the RFID transponder 30 and the RFID reader 32 between the devices of the system 200 as described herein. Power can also be communicated or transmitted there between as aforementioned. Communication of information, signals and/or power may include two-way communication or one way communication from one component to another component of the system 200 in non-limiting embodiments, as described above. Communication of information can also or alternatively be provided by way of Bluetooth connection 34 as shown in the non-limiting embodiment of FIG. 2. The medicament device 10b may further include a sensor 28, and a transmitter 36 to send a signal from sensor inputs, for example, to the collateral device 12b. The collateral device 12b may include an information detecting component 16, an information receiving component 18, a signal output component 26, a storage medium component 22, a microprocessor 20, and a power source, in on-limiting embodiments. The collateral device may also include an information sending component to send information to the medicament device 10b, in a non-limiting embodiment.

Embodiments of the system described herein, such as, in a non-limiting example, the system of FIG. 2 provide communication between a medicament device 10b and a collateral device 12b, wherein the collateral device may include a Smartphone or other such device which may include some of the various components described.

Embodiments of the medicament system provided herein, for example, as in FIG. 2 may be used to train a user to use the medicament device, wherein feedback about a use of the device, about a medicament, or about a user, for example, may be provided by the collateral device. Furthermore, the medicament system embodiments may be used to guide a user to deliver medicament or train a user to use a medicament device, wherein the user is a training-only or training and deliver device, by providing feedback to the user on the collateral device 12b, in a non-limiting embodiment. Consequently the connection between the medicament device 10b and the collateral device 12b can provide a communication of information such that the collateral device 12b may be used to communicate information about the medicament device 10b or a user thereof to the user, in non-limiting embodiments.

Figure 3:
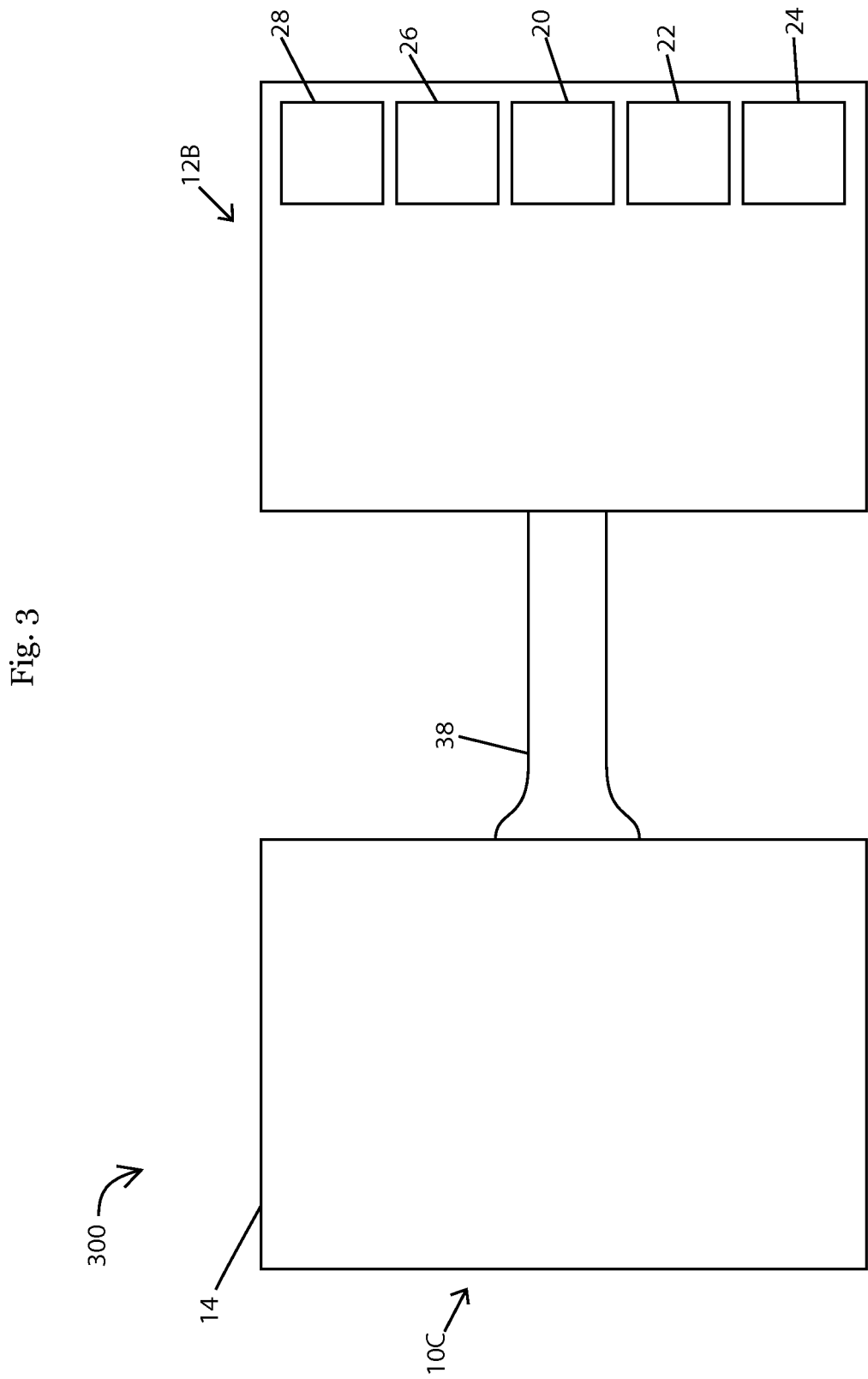
FIG. 3 is a schematic of a further system embodiment described herein.

In a further embodiment, a medicament system embodiment 300 is provided in FIG. 3, wherein a medicament device 10c including a housing 14 is configured to be attached to a collateral device 12c (or vice versa, the collateral device 12c may be configured to be attached to a medicament device 10c) by way of an attachment component 38, in a non-limiting embodiment. The collateral device 12c may include a sensor 28, a signal output component 26 to communicate and provide feedback to a user, a microprocessor 20 to process signals received from the sensor 28 in anon-limiting embodiment, a storage medium component 22, and a power source 24 to provide power to the collateral device 12c and, in further non-limiting embodiments, to the medicament device 10c by way of wired or wireless connections as described herein. In the medicament system embodiment 300, the medicament device 10c may have, but need not include any components, wherein all the system components may be in the collateral device 12c. Information can be sensed by and/or received by the collateral device 12c from the medicament device 10c (and in some embodiment sent to the medicament device 10c from the collateral device 12c), via the attachment between the collateral device 12c and medicament device 10c through the attachment component 38.

Figure 4:
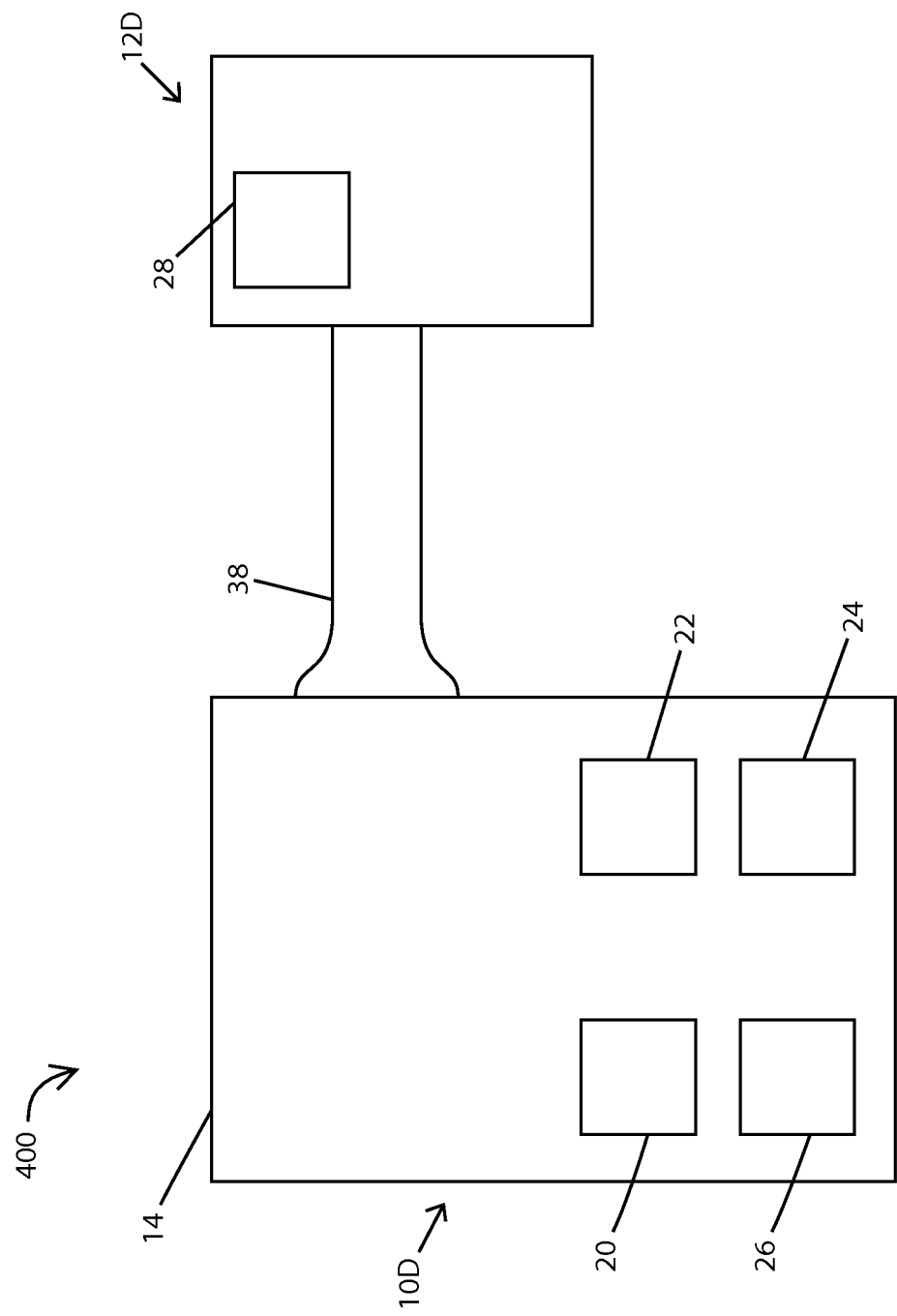
FIG. 4 is a schematic of yet another system embodiment described herein.

In still a further embodiment of the medicament system 400 shown in FIG. 4, the medicament device 10d and the collateral device 12d may be configured to be attached to one another by way of an attachment component 38. The collateral device 12d may include a sensor 28, and the medicament device may include a housing 14, a microprocessor 20, a storage medium component 22, power source 24, and signal output component 26. In this embodiment the power source may be used to power the collateral device 12d by way of a wired or wireless connection between the medicament device 10d and collateral device 12d.

Figure 5:
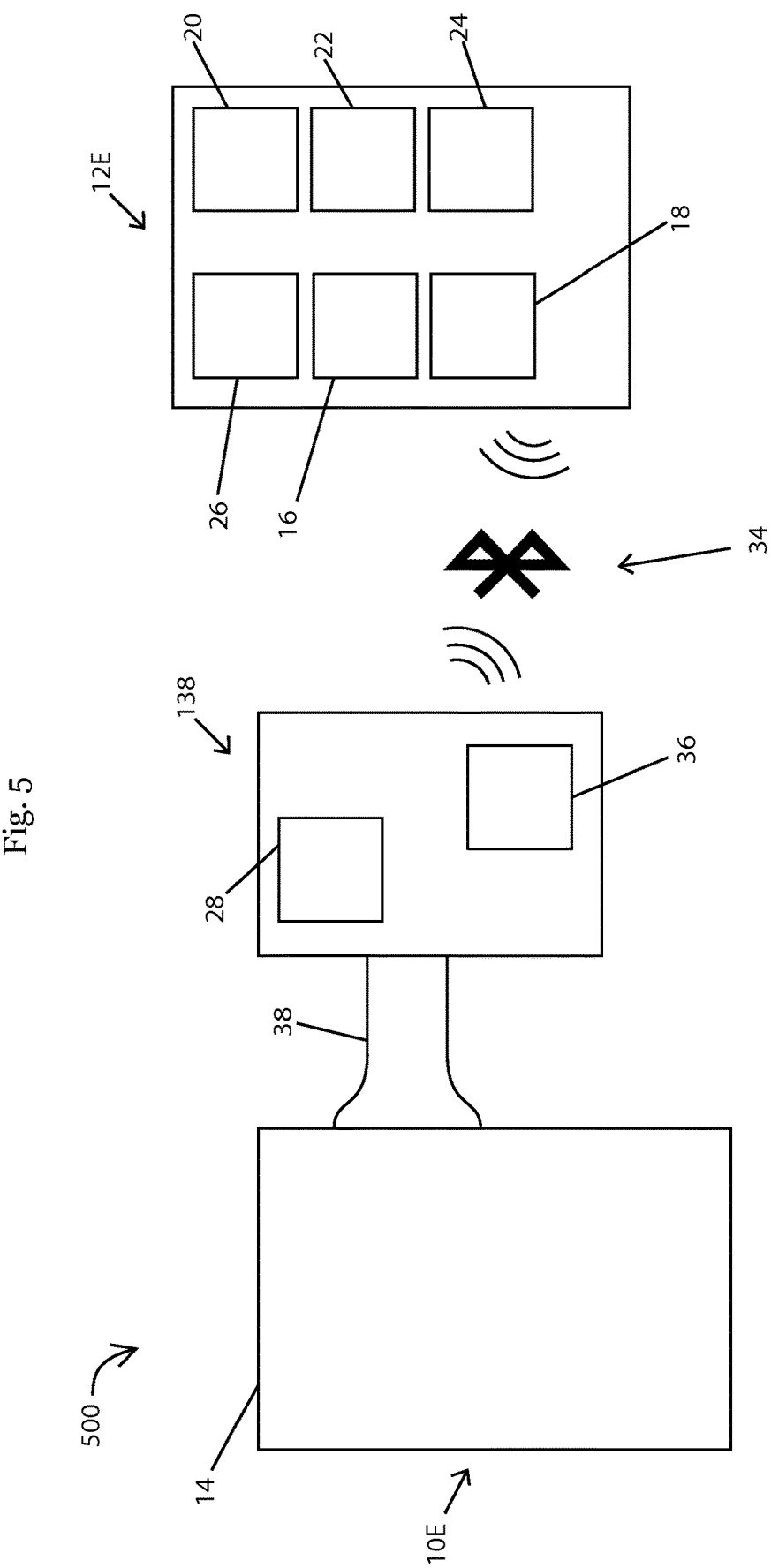
FIG. 5 is a schematic of a system embodiment described herein.

In yet a further embodiment of the medicament system 500 shown in the schematic of FIG. 5, a medicament device 10e having a housing 14 and an intermediate collateral device 138 are configured to be attached to one another by way of an attachment component 38. The intermediate collateral device 138 may include a sensor 28 to sense information about the intermediate collateral device 138 and therefore, the medicament device 10e by way of its attachment thereto. Sensor information can include location information, position, orientation, among other information as described herein that can be sensed by one or more sensors of the system. The medicament system embodiment 500 may further include a collateral device 12e, which may include other components of the system such as, for example, the signal output component 26, the information detecting component 16, information receiving component and/or sending component 18, microprocessor 20, storage module 22, and/or power source 24, in a non-limiting embodiment. The collateral device 12e may be associated with the intermediate collateral device 138 by way of a wired and/or a wireless connection as described herein, for example, by a Bluetooth® connection 34. Furthermore, in a further non-limiting embodiment, the collateral device 12e may connect wirelessly or by wired connection with the medicament device 10e.

Figure 6:
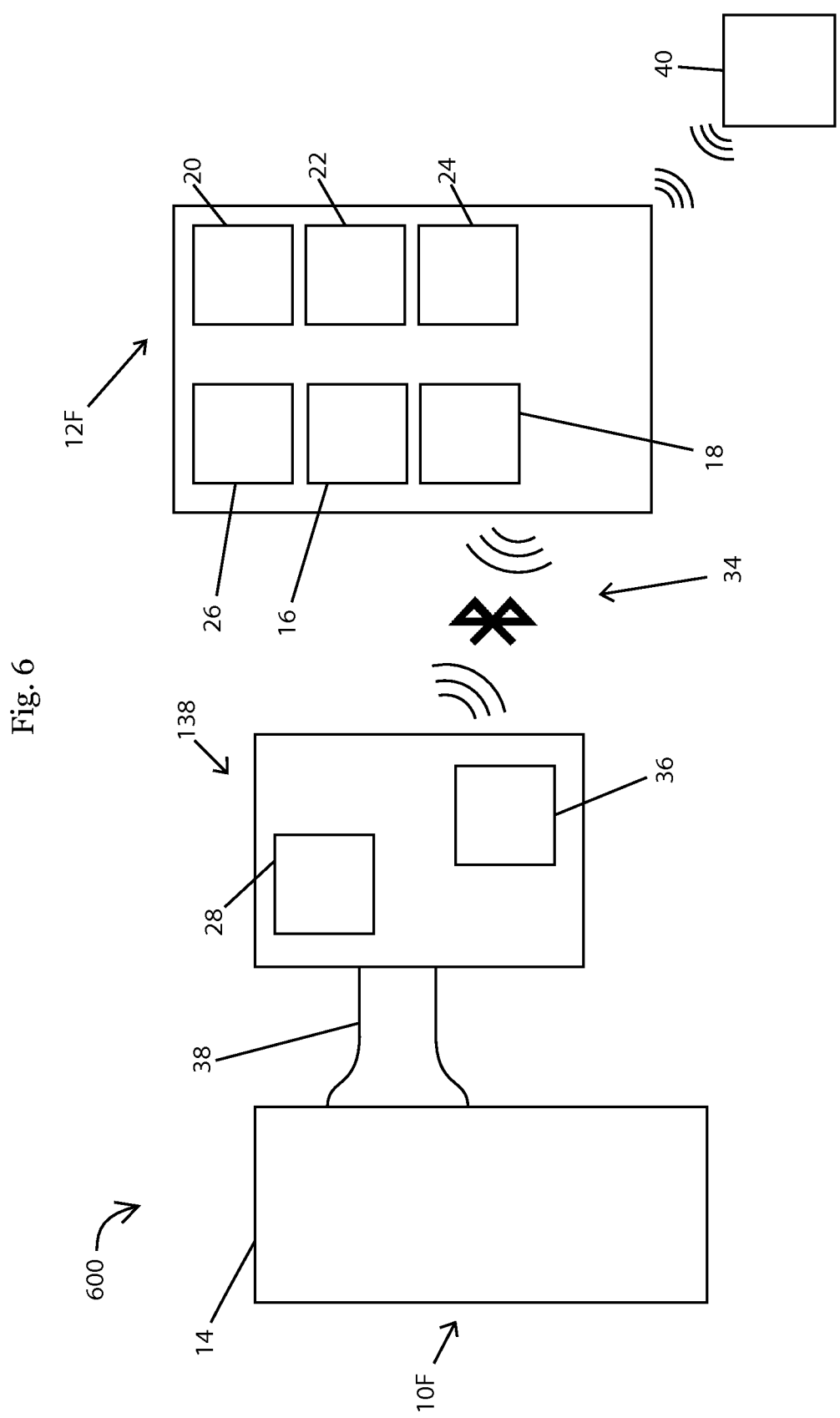
FIG. 6 is a schematic of a system embodiment described herein.

In yet a further embodiment of the medicament system 600 shown in FIG. 6, a medicament device 10f may be associated with an intermediate collateral device 138. The association between the medicament device 10f and the intermediate collateral device 138 may include a wired or a wireless connection, or may include an attachment component 38 as shown in FIG. 6. The intermediate collateral device 138 may further be communicatingly connected to a collateral device 12f. The collateral device 12f may be further communicatingly connected to a remote device 40. The connections between the devices of the system 600 may include wired or wireless connection as described herein, the wireless connection including but not limited to RFID or Bluetooth® connection. The remote device 40 may include a database to which information can be uploaded to from the system 600 or downloaded from to the system 600. The remote device 40 may further include another device, a computer, a telephone, a smart device, or a watch, among other devices. These devices may allow other persons or entities to send information to the system 600, retrieve information from or receive information from the system 600, in non-limiting embodiments. Additionally, in the embodiment of 600, the intermediate collateral device 138 or the medicament device 10f may be configured so as to send information to or receive information from the remote device 40, by either wired or wireless communication as discussed herein.

Figure 7A:
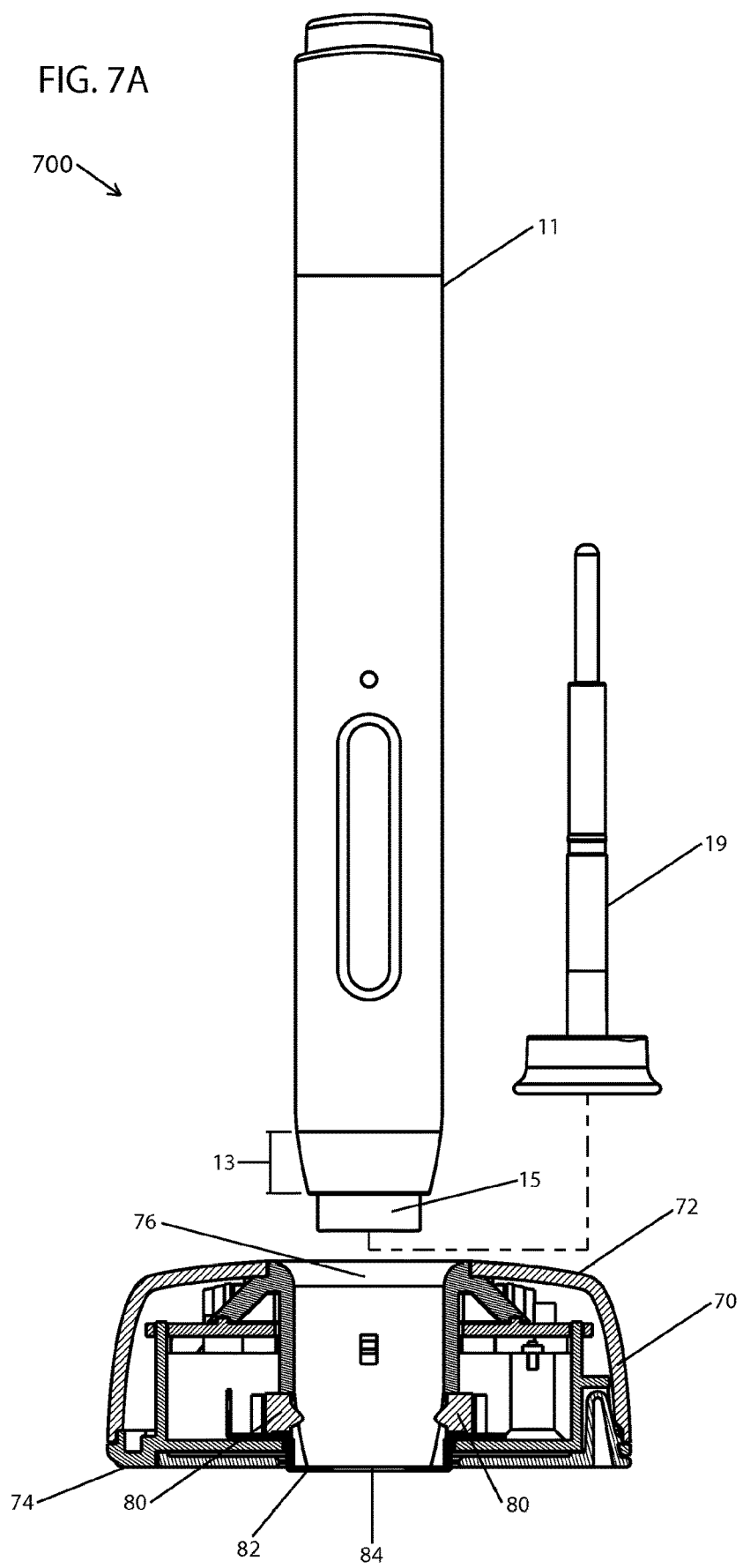
FIGS. 7A-7E include views of an embodiment of a system described herein, wherein a collateral device is shown in cross-sectional view.
Figure 7B:
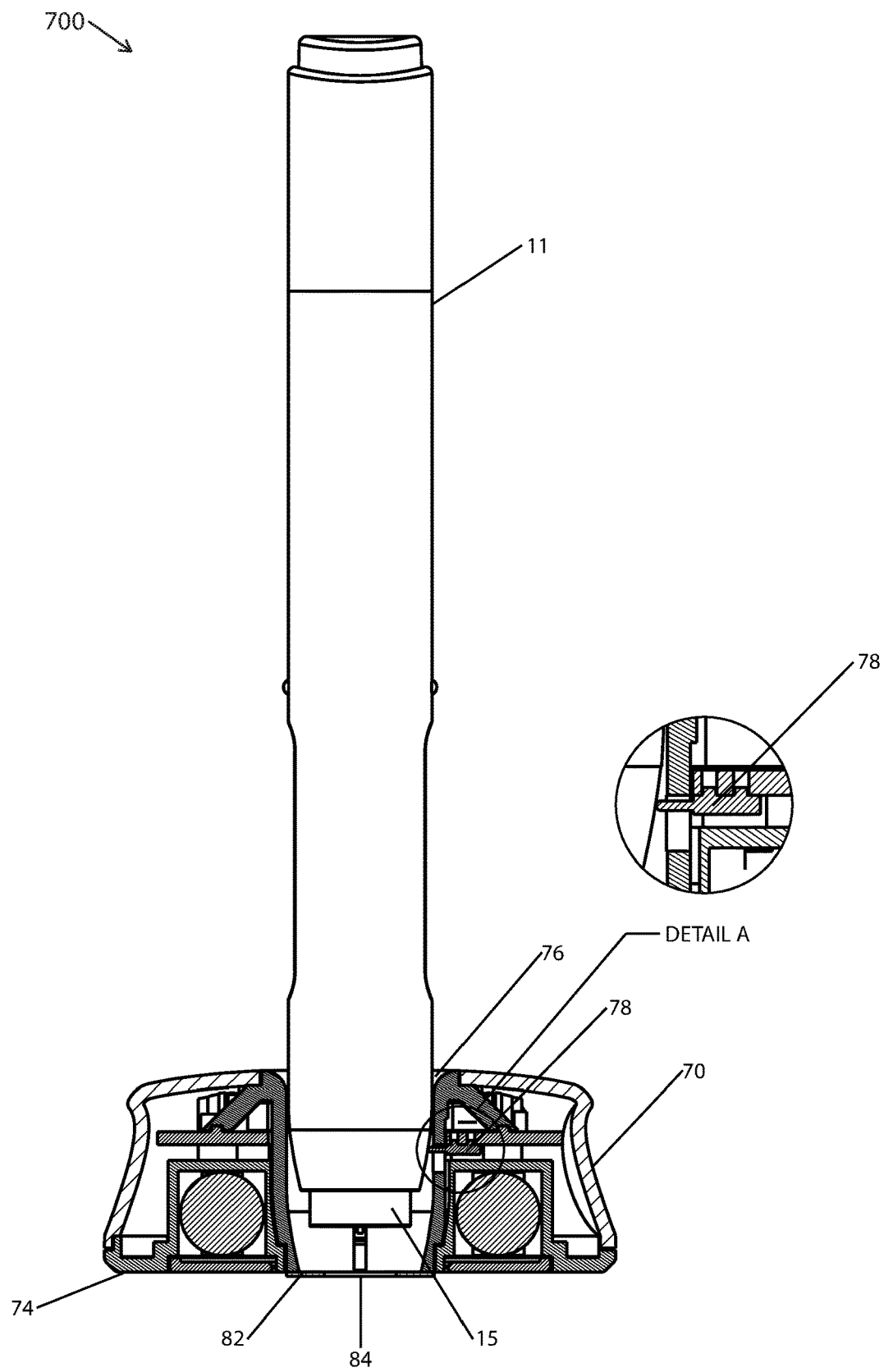

FIG. 7A is a side view of an embodiment of a medicament system 700 configured to receive and/or communicate information about the system, about a medicament device, or about a use of the medicament device, or a combination thereof to a user. The medicament system 700 includes a medicament device 11 having a housing, a removable cap 19, a distal end 13, and a retractable safety shield 15. In one non-limiting embodiment, the distal end 13 may include a tapered shape as shown in FIG. 7A. The system 700 further includes a collateral device 70, shown in cross-sectional view in FIG. 7A, including a top portion 72, a bottom portion 74, an opening 76 for receiving a portion of the medicament device 11, at least one sensor 80, 82, an injection member aperture 84. FIG. 7A shows the medicament device 11 with the cap removed 19 prior to insertion into the opening 76. In the embodiment 700 shown in FIG. 7A, the sensor 82 forms a portion of the bottom portion of the collateral device. The sensor 82 is a capacitive sensor, embodied as a plate, and configured to detect placement of the collateral device against the skin of a user, and/or detect contact with a portion of the medicament device 11 once fully inserted into the collateral device 70 (i.e., to detect contact with the safety shield or distal end 13 of the medicament device housing. As shown in the side view of FIG. 7B, the medicament device 11 is further inserted into the opening 76 of the collateral device 70. FIG. 7B shows a cross-sectional view of the collateral device from a point of view rotated approximately 90 degrees from the view seen in FIG. 7A.

Figure 7C:
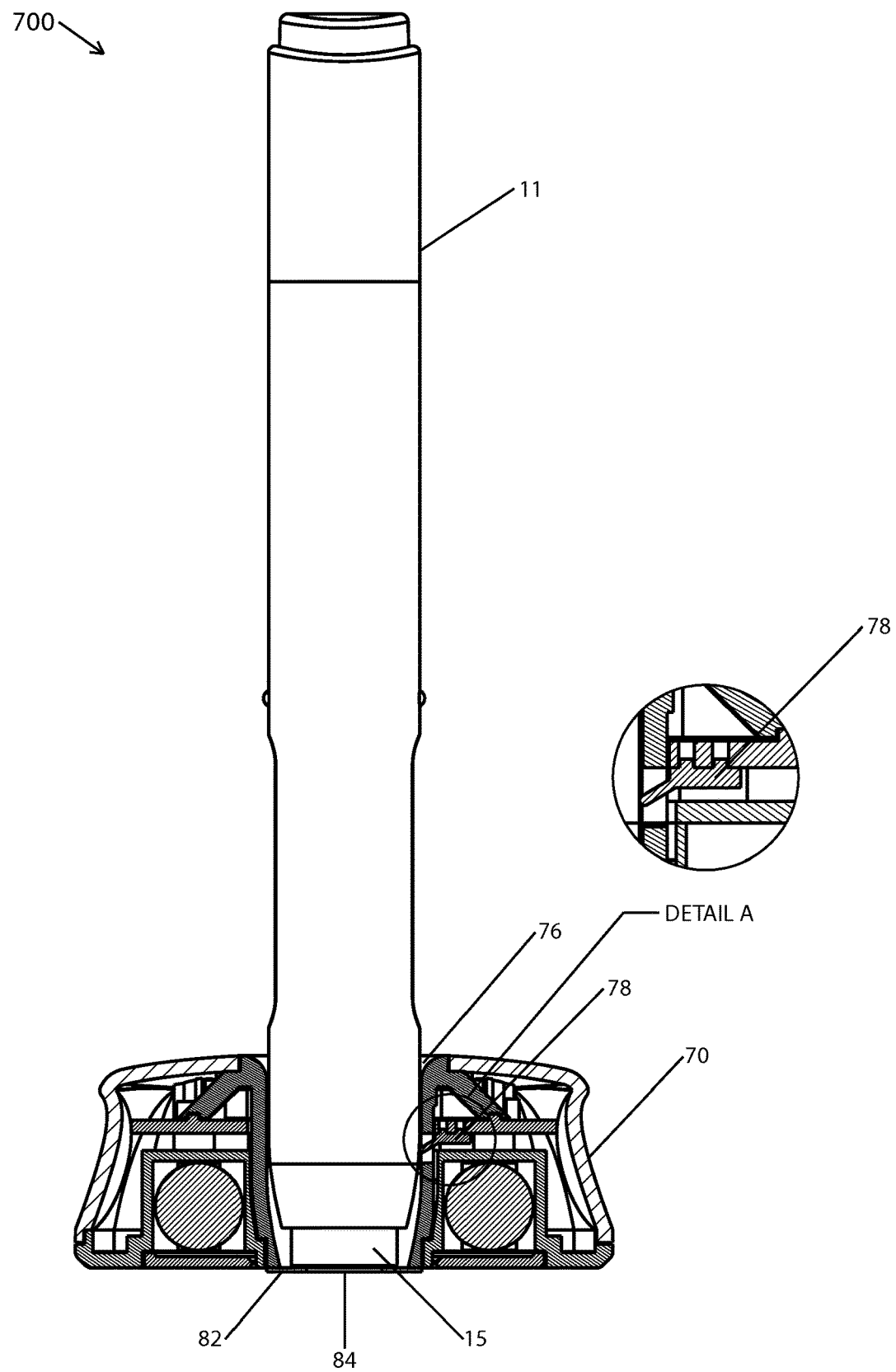
Figure 7D:
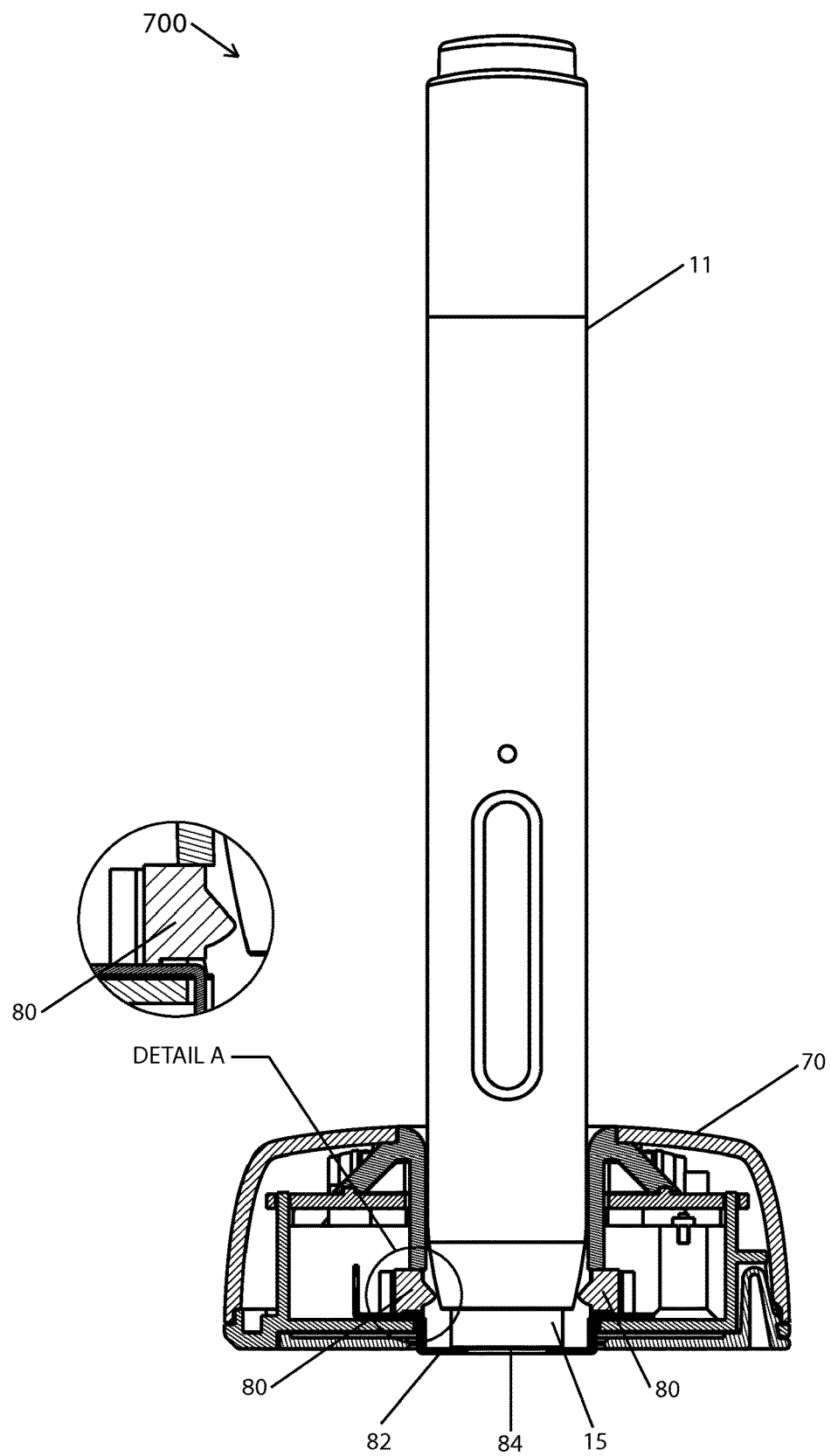
Figure 7E:
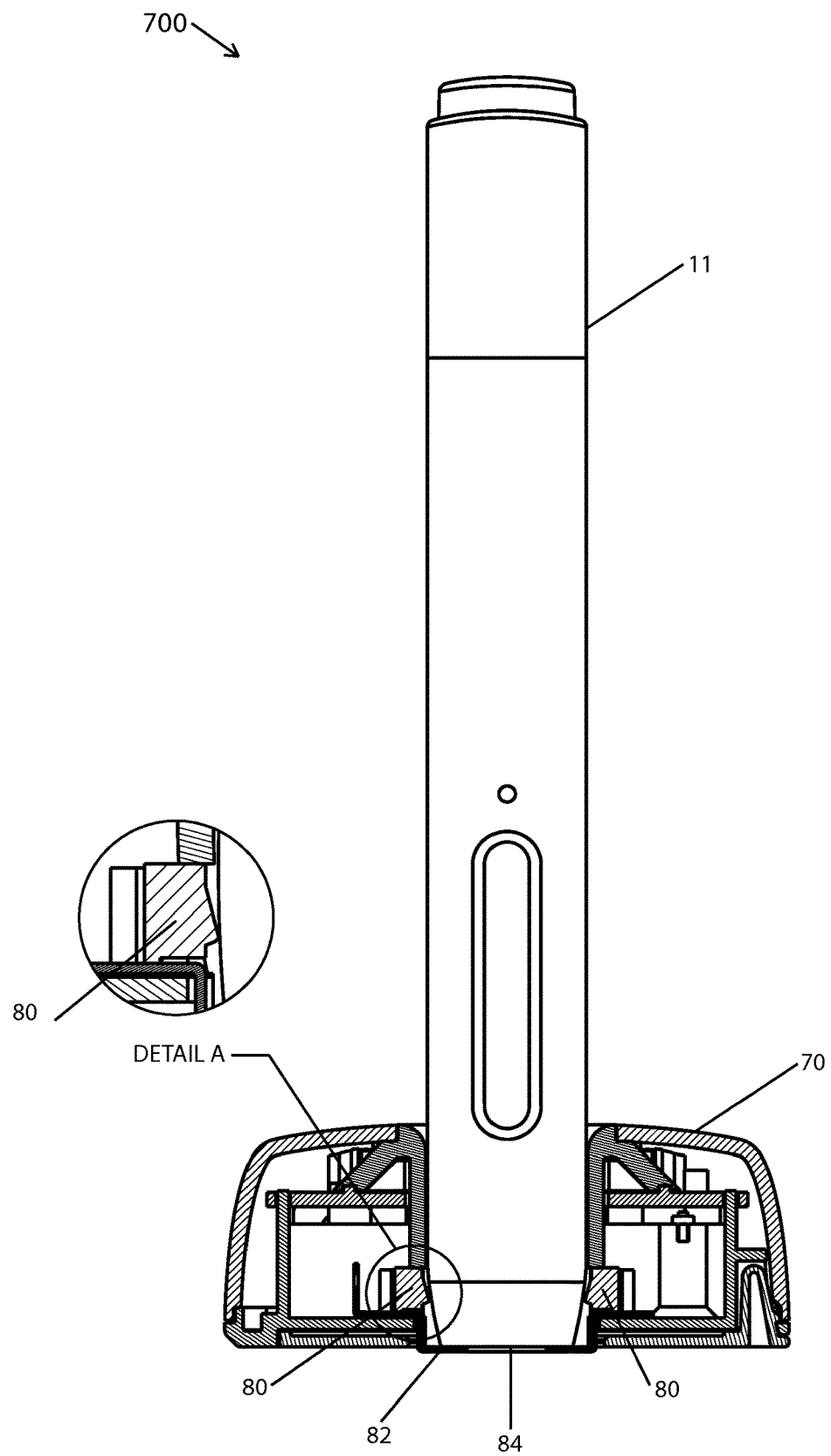

The view of FIG. 7B shows another sensor 78 of the collateral device, adjacent to the opening 76, wherein the sensor 78 detects insertion of the medicament device without cap 19, due to the contact between the sensor and the distal end of the medicament device 11. If the medicament device 11 were inserted with cap 19 on the device, there would not be contact between the sensor 78 and the distal end of the medicament device 11, and therefore, the sensor 78 would not sense contact with the medicament device 78. This may produce an error in the system, for example, which may be output via a signal output component shown in FIG. 7F, or no indication to a user at all, in non-limiting examples. Upon proper removal of the cap 19 and insertion of the medicament device 11 into the opening 76 as shown in FIG. 7B, contact is made with the sensor 78, and a signal output may be provided to a user. Sensor 82 may sense contact between the collateral device and the skin of a user, and a signal output may be provided to indicate the status of the system in a non-limiting embodiment. Further insertion of the medicament device 11 into the opening 76 of the collateral device 70, as shown in FIG. 7C, shows movement of the sensor 78 (i.e., a mechanical switch in one non-limiting embodiment as shown) to a second position, as the medicament device safety shield 15 reaches the bottom portion of the collateral device 70 housing. The injection member aperture 84 is shown in FIG. 7C. FIG. 7D shows a 90 degree rotation of the collateral device, wherein the sensors 80 for sensing depression of the safety shield (shown in FIG. 7A), are not yet in contact with the distal end 13 of the medicament device 11. The injection member aperture 84 within the sensor 82, which forms part of the lower portion of the collateral device is shown. The needle shield 15 is not yet depressed. FIG. 7 E provides a view of the system 700 shown in FIG. 7D, wherein the medicament device 11 is inserted into the collateral device 70, and the safety shield 15 (not shown) is depressed (i.e., fully retracted within the medicament device 11). The system 700 detects retraction of the safety shield, as the sensor 80 contacts the medicament device 11 as shown in FIG. 7E, activating the sensor 80. Aperture 84 is shown in the sensor (i.e., plate) 82.

Figure 7F:
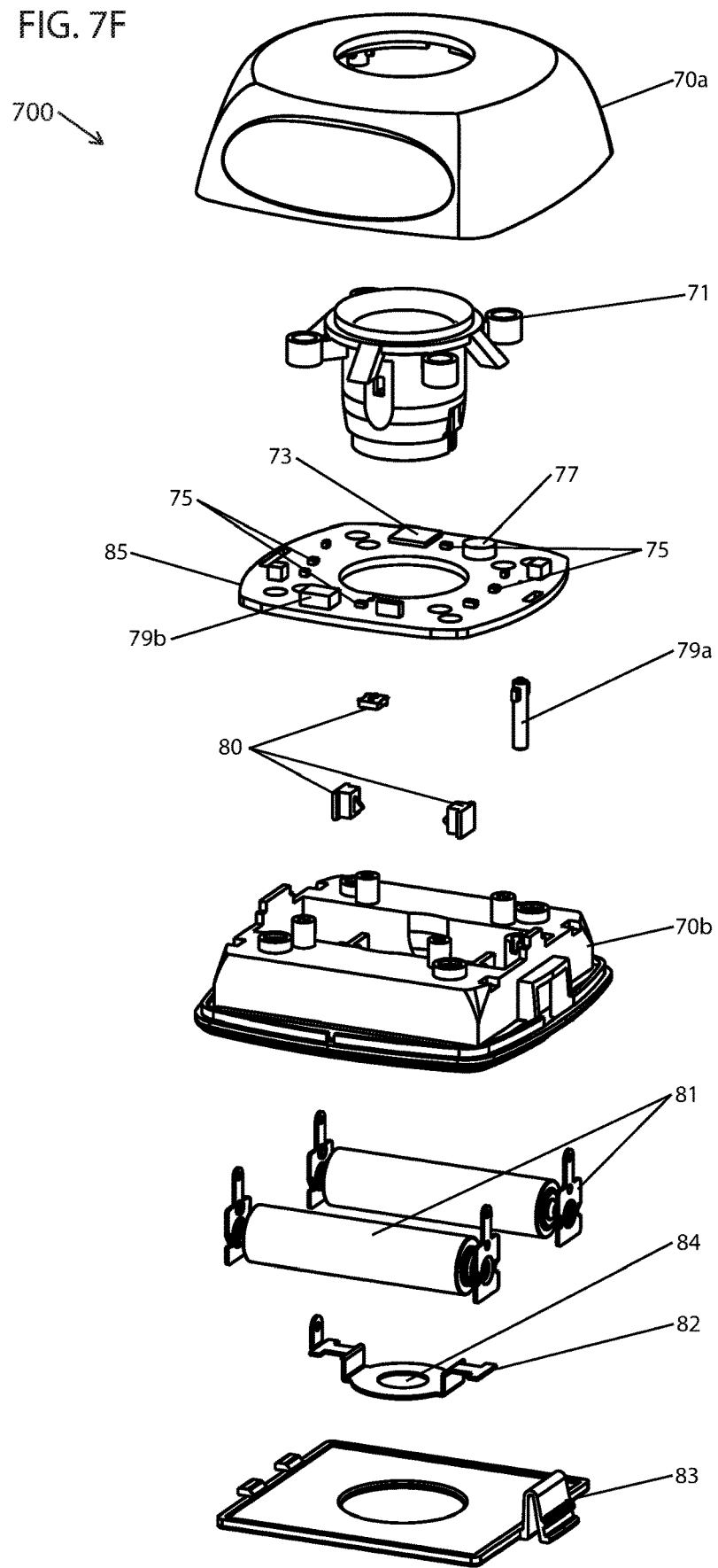
FIG. 7F is an exploded view of the collateral device embodiment shown in FIGS. 7A-7E.

FIG. 7F shows an exploded view of the components of the collateral device 70 of the embodiment 700. A top housing portion 70a of the collateral device housing is provided, as well as a light pipe 71 which is configured to direct light from any light source provided on a printed circuit board assembly 85 located there below. For example, the signal output component 75 may include light (i.e., light emission diode (LED), for example). When the collateral device is assembled, the light from the LEDs 75 may be directed via light pipe 71 to a user of the system. The lights may be provided to a user as a form of feedback before, during or after use of the system, in one non-limiting embodiment. The lights may also provide indication of powering on or off of the system or the collateral device 70, in other non-limiting embodiments. In further non-limiting embodiments, as discussed herein, the signal output component 75 may include lights, and/or an audio component, such as a speaker, for example, to provide audio feedback to a user, any other type of signal output component 75 described herein or known to those skilled in the art.

The printed circuit board assembly 85 may further include a microprocessor 73, an information detecting/receiving component, such as a microphone 77 to receive sounds from the medicament device 11, and a blue tooth transmitter 79*b* in one non-limiting embodiment, which works in conjunction with a blue tooth pairing button 79*a* used to pair the collateral device to another device. The blue tooth components 79*a*, 79*b* may be used to sync the device 70 and/or system to other devices, to phone applications, or to transmit information or receive information to/from the medicament device, other medicament devices, other collateral devices or other transmitting/receiving components or databases. The microphone 77 may be used to detect sounds of the medicament device 11 including movement of the medicament device or the components there of relative to one another to indicate a status of the medicament device 11, such as, for example, removal of the cap 19, contact of the safety shield, depression of the safety shield, delivery of the injection member, insertion of the injection member into the target area, delivery of medicament, completion of delivery of medicament, retraction of the injection member, extension of the safety shield, and other such sounds indicating a status of the medicament device 11.

The sensors 80 are shown as contact switches in the exploded view of FIG. 7F, these may also be embodied as other sensor types described herein. The bottom housing 70*b* of the collateral device is shown, as well as the power source 81 shown as batteries in the embodiment provided herein. Other types of power sources may additionally or alternatively be used. The sensor 82 with injection member aperture 84 is provided. In one non-limiting embodiment, the sensor 82, may include a capacitive contact plate as described herein. As known to those skilled in the art, a capacitive contact sensor or contact plate may determine contact against a surface (i.e., target surface like the skin of a user), by detecting resistance. A power source housing cover 83 is shown in FIG. 7F.

Figure 8A:
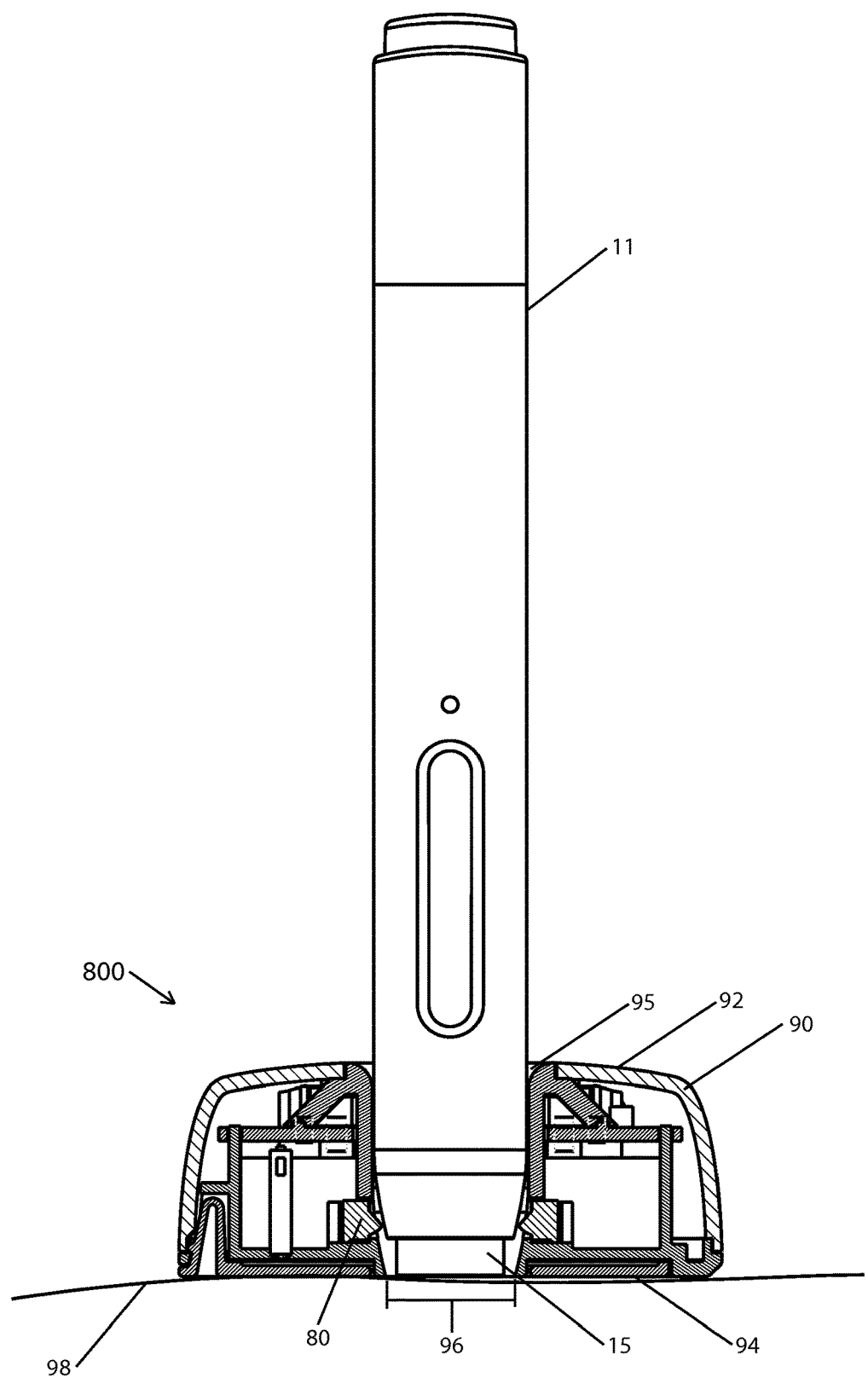
FIGS. 8A-B are views of another embodiment of a system described herein, wherein a collateral device is shown in cross-sectional view.
Figure 8B:
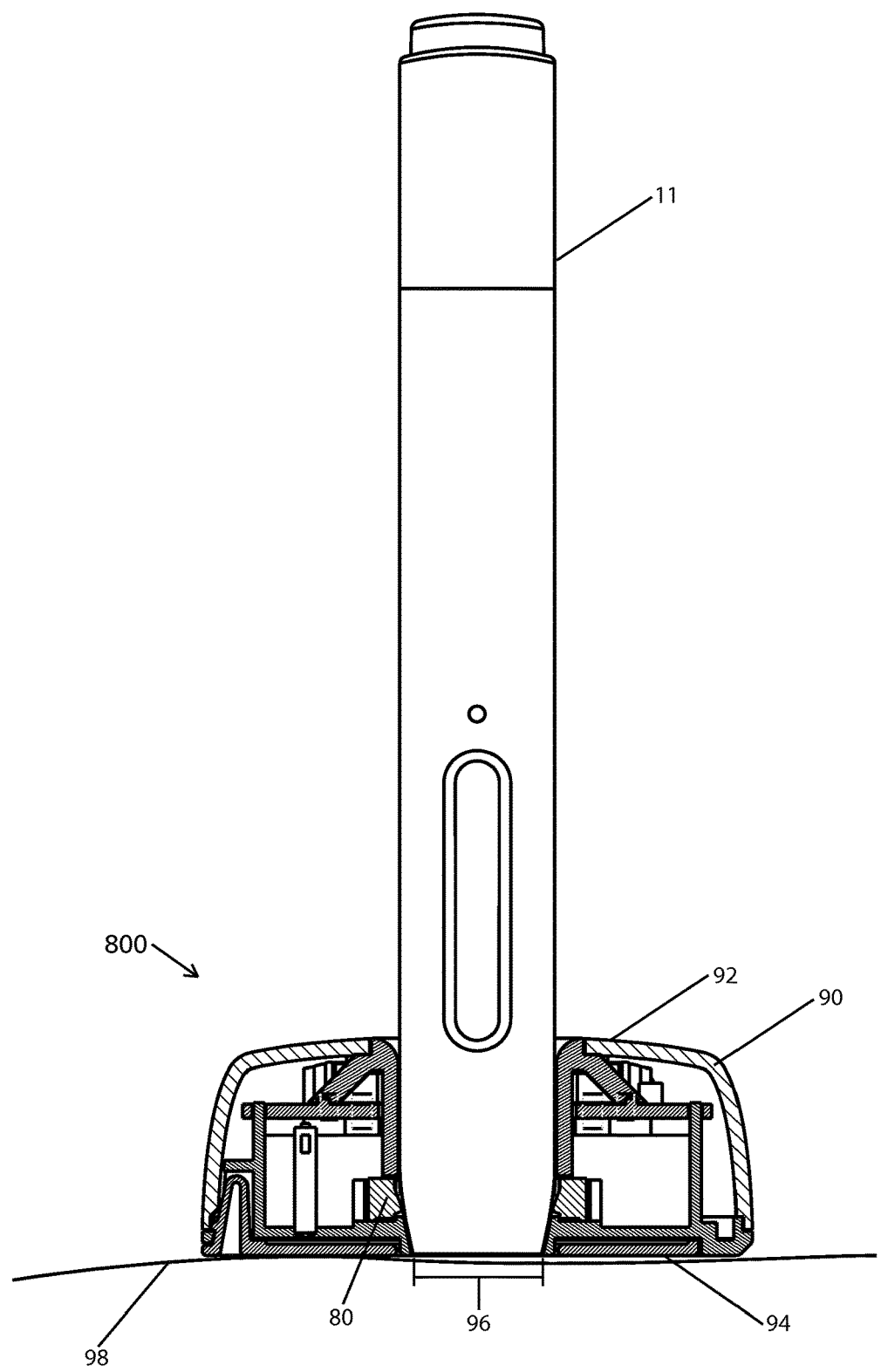

FIG. 8A-8B include a further embodiment 800 of the medicament system, wherein the collateral device 90 includes a top portion 92, a bottom portion 94 for resting against a target area 98 of a user. The collateral device 90 further includes an opening 95 for receiving at least a portion of a medicament device 11. The medicament device 11 may include a safety shield 15 and an injection member (not shown). The collateral device 90 may include a safety shield opening or aperture 96 in the bottom portion 94 configure to receive the distal end of the injection device 11. The sensors 80 are also provided in the embodiment 800 of the system. Sensors 78 as described above may also be provided in this embodiment (not shown). The sensors may detect removal of the cap of the medicament device 11, depression of the needle shield (as shown in FIG. 8B) wherein eh contact sensor or contact switch 80 contacts the medicament device 11, and further sensors may be provided to indicate contact with the collateral device and the target area of the user, for example. In this embodiment, the medicament device 11 may directly contact the skin of the user via the opening 96, and the injection member may be ejected to deliver medicament to a user. Feedback may be provided to the user about use of the medicament device and/or collateral device of the system via signal output components as described above in regard to the embodiment 700 of FIG. 7.

Figure 8C:
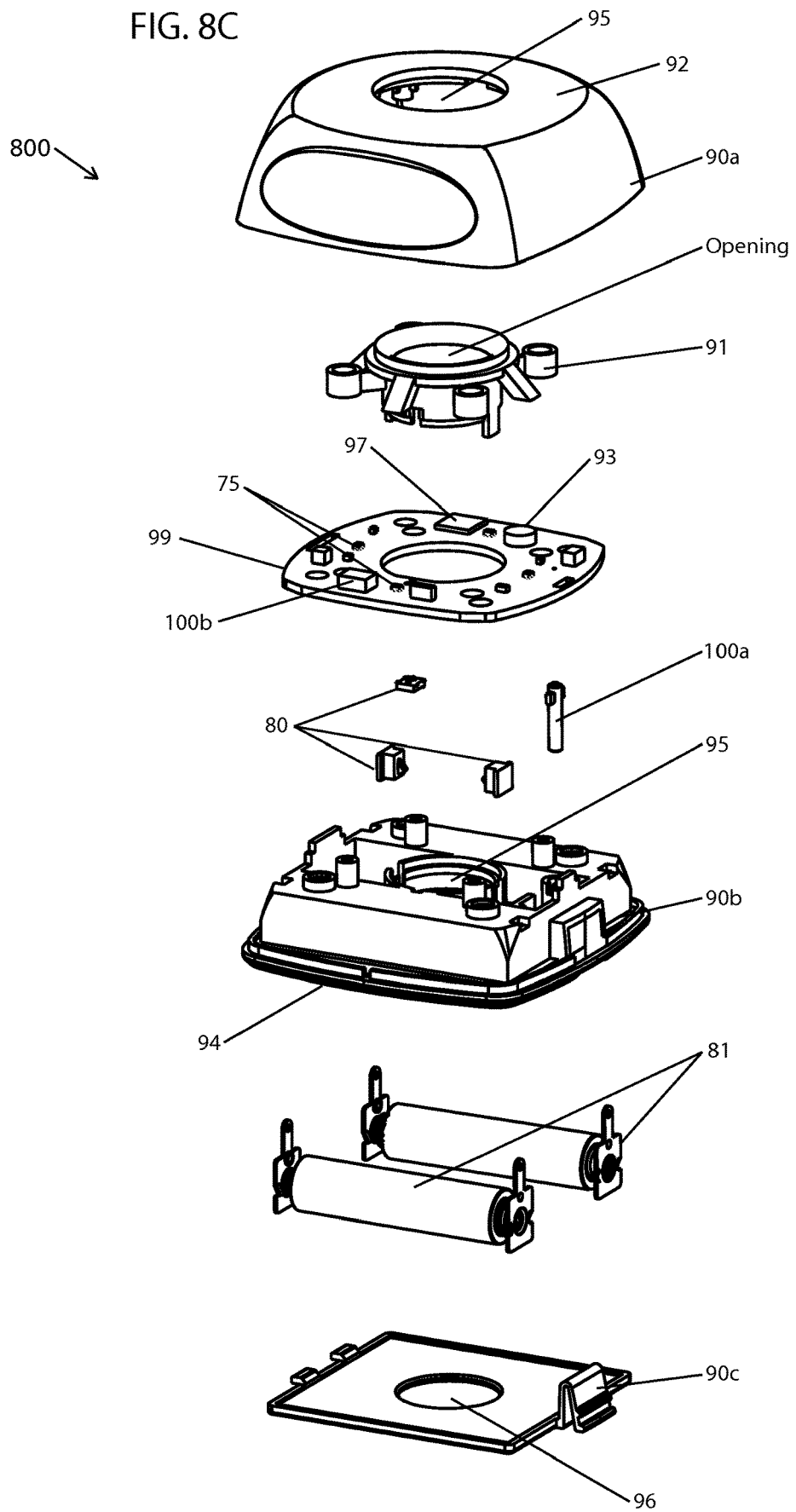
FIG. 8C is an exploded view of the collateral device embodiment shown in FIG. 8A-B.

FIG. 8C shows an exploded view of embodiment 800 of the system showing the collateral device upper housing 90*a* with an opening 95 for the medicament device 11, the upper housing 90*a* having an upper portion 92, and lower housing 90*b* having a bottom portion 94 is also provided. A light pipe 91 configured to direct light from the collateral device 90 is shown. A microprocessor 97, a microphone 93, a signal output component 75 (which may include LED, or speaker, or other signal output component) and a blue tooth transmitter 100*b* are provided, and may be provided on a printed circuit board assembly 99, in a non-limiting embodiment as shown. A storage medium may be further provided in this embodiment. A power source 81 is shown as well as a power source compartment cover 90*c* having a safety shield aperture 96 for allowing the safety shield to traverse the collateral device 90 to contact the target area of the user during use.

Figure 9E:
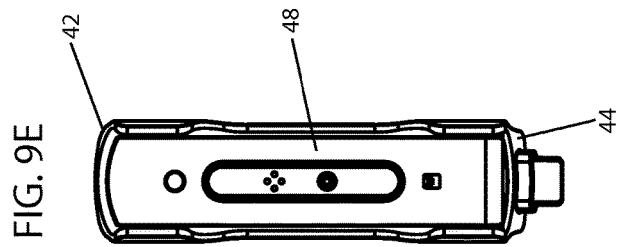
FIG. 9A-E are various side, top, bottom, front and back views of an embodiment of a collateral device.
Figure 9B:
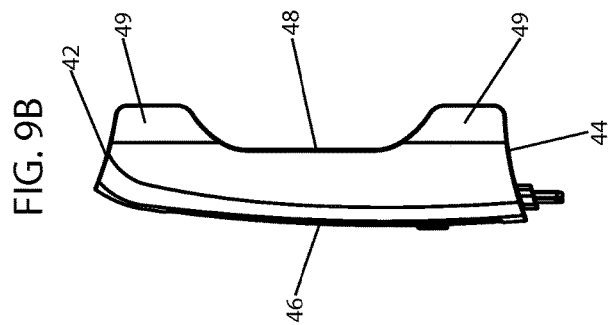
Figures 9A, 9C:
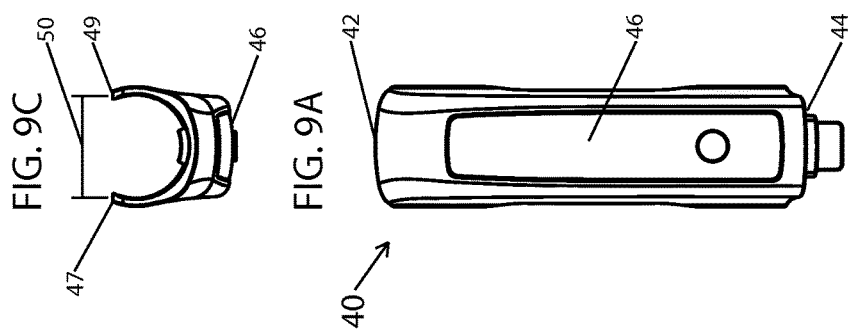
Figure 9D:
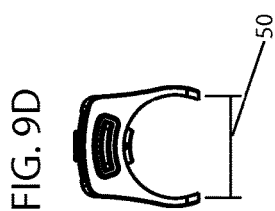
Figure 9F:
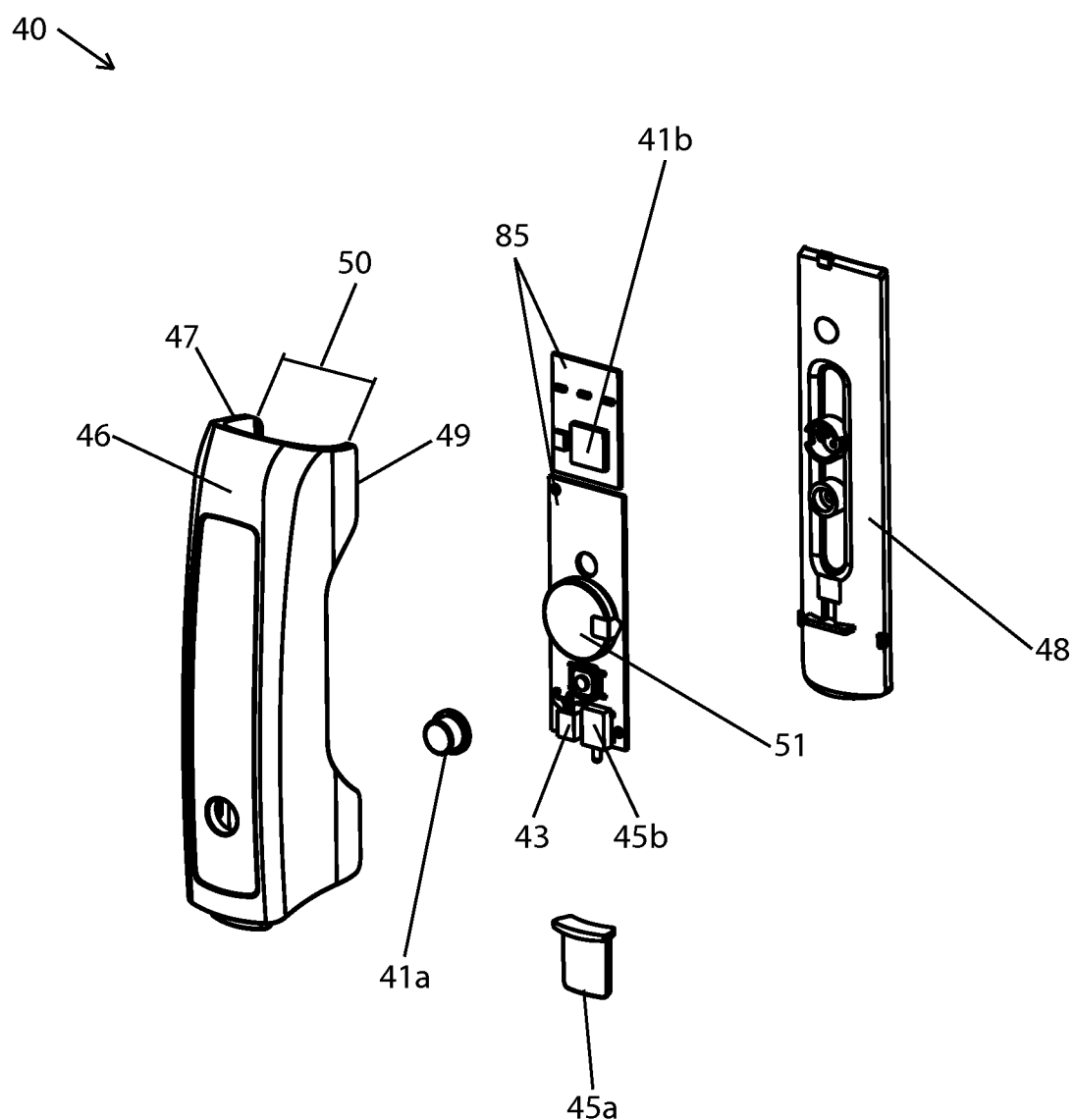
FIG. 9F is an exploded view of the collateral device embodiment shown in FIGS. 9 A-E.
Figure 9G:
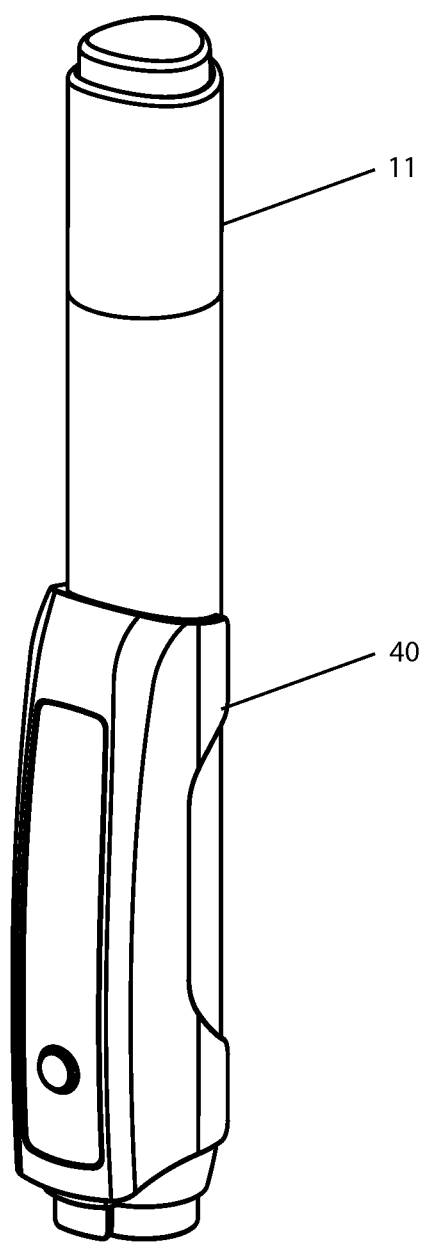
FIG. 9G is a perspective view of the collateral device embodiment shown in FIGS. 9A-F attached onto a medicament device.

In a further embodiment of the collateral device 40 shown in FIGS. 9A-G, an outer surface 46, an inner surface 48, a top side 42, a bottom side 44, a first end 49 and a second end 49 are provided. A contact element 45 is associated with the bottom side 44 of the collateral device embodiment 40. An attachment component 50 is shown as a combination of the inner surface 48 and the first and second ends 47, 49 of the collateral device 40, in the embodiment shown. The attachment component, as further described herein, may include other forms of attachment, such as an adhesive, a hook and loop fastener, a clip, or as shown in the embodiment of the collateral device 40, a particular shape of the housing corresponding to a shape of the medicament device upon which the collateral device may be attached. The attachment component may include a portion of the housing that is complementary in shape to a portion of the housing of the medicament device as provided in the embodiment of FIGS. 9A-G. FIG. 9G shows attachment of the collateral device 40 onto the medicament device 11. The attachment may be permanent or non-permanent. The collateral device may snap onto the medicament device 11, in a non-limiting embodiment, during use of the medicament device 11, and may be removable and reusable for another medicament device 11.

The collateral device 40 may further include a blue tooth pairing component 41*a*, a blue tooth transmitter 41*b*, a microphone 43, a power source 51, and some or all of these components may be associated with a printed circuit board assembly 85 as shown herein. The collateral device 40 may further include one or more signal output components to provide information and/or feedback to a user. The microphone 43 may receive sounds from the medicament device 11 during use, and may be used to identify a status of the medicament device 11 as described in other embodiments herein, such as movement of one or more components of the medicament device relative to one another during use of the medicament device. Another example may include a sound that indicates completion of delivery of medicament from the medicament device, which may be picked up by the microphone 43 component, for example. The collateral device embodiment 40 may include a contact element 45a that may interact with a contact switch 45b, in a non-limiting embodiment shown in the exploded view of FIG. 9F. The contact element 45a and contact switch 45b may interact with one another to indicate a contact with the medicament device 11 and the target area of the user and further, to indicate deflection of the safety shield of the medicament device, wherein upon deflection of the safety shield, the contact element 45a is pressed against the target area of the user, and is displaced in a direction toward the contact switch 45b to activate the contact switch 45b. The collateral device 40 may register the status of the medicament device 11. The collateral device 40 may also provide feedback to a user via a signal output component regarding the status of the medicament device 11.

Figure 10A:
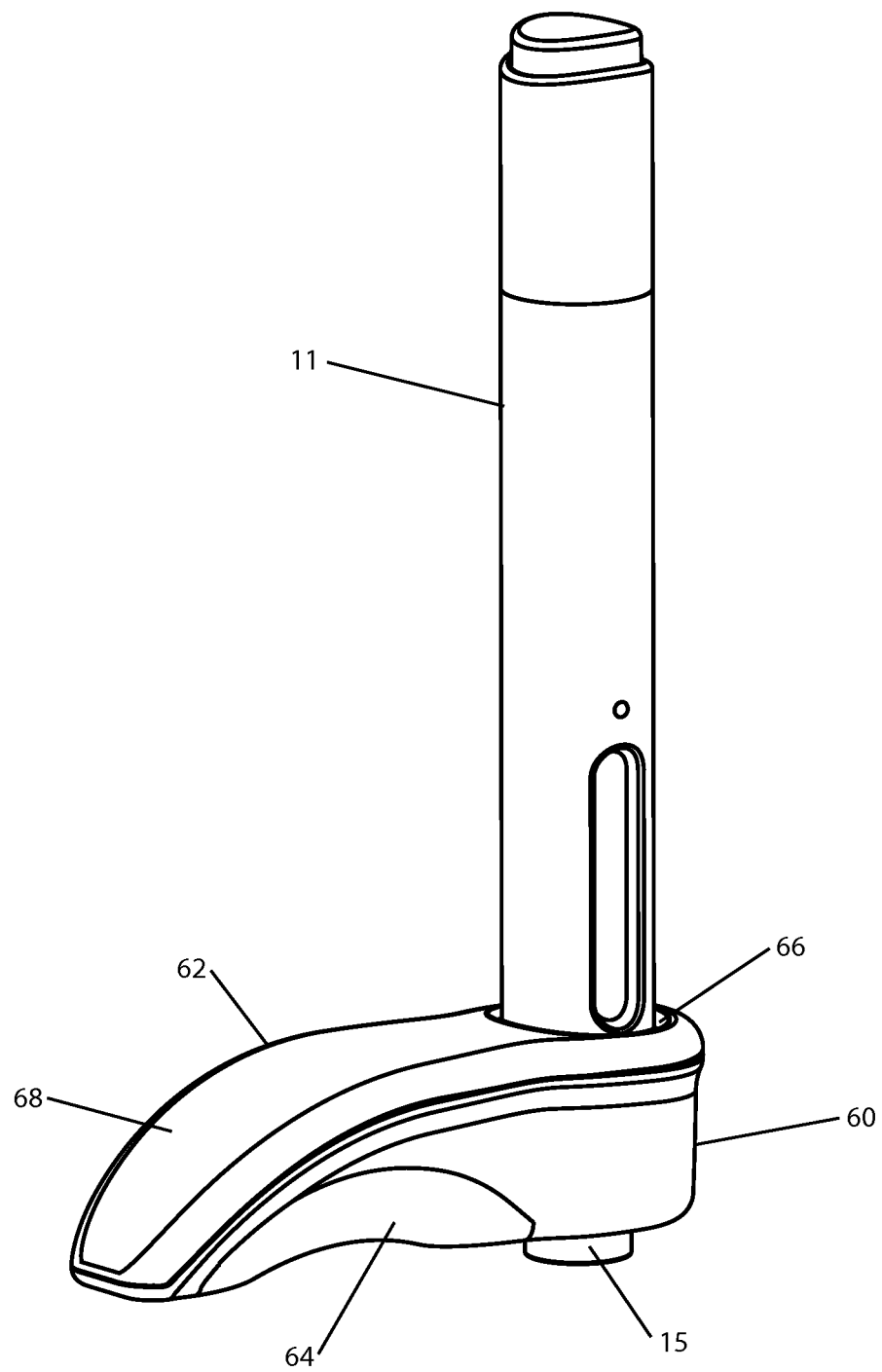
FIG. 10A is a perspective view of another embodiment of a collateral device associated with a medicament device.
Figure 10B:
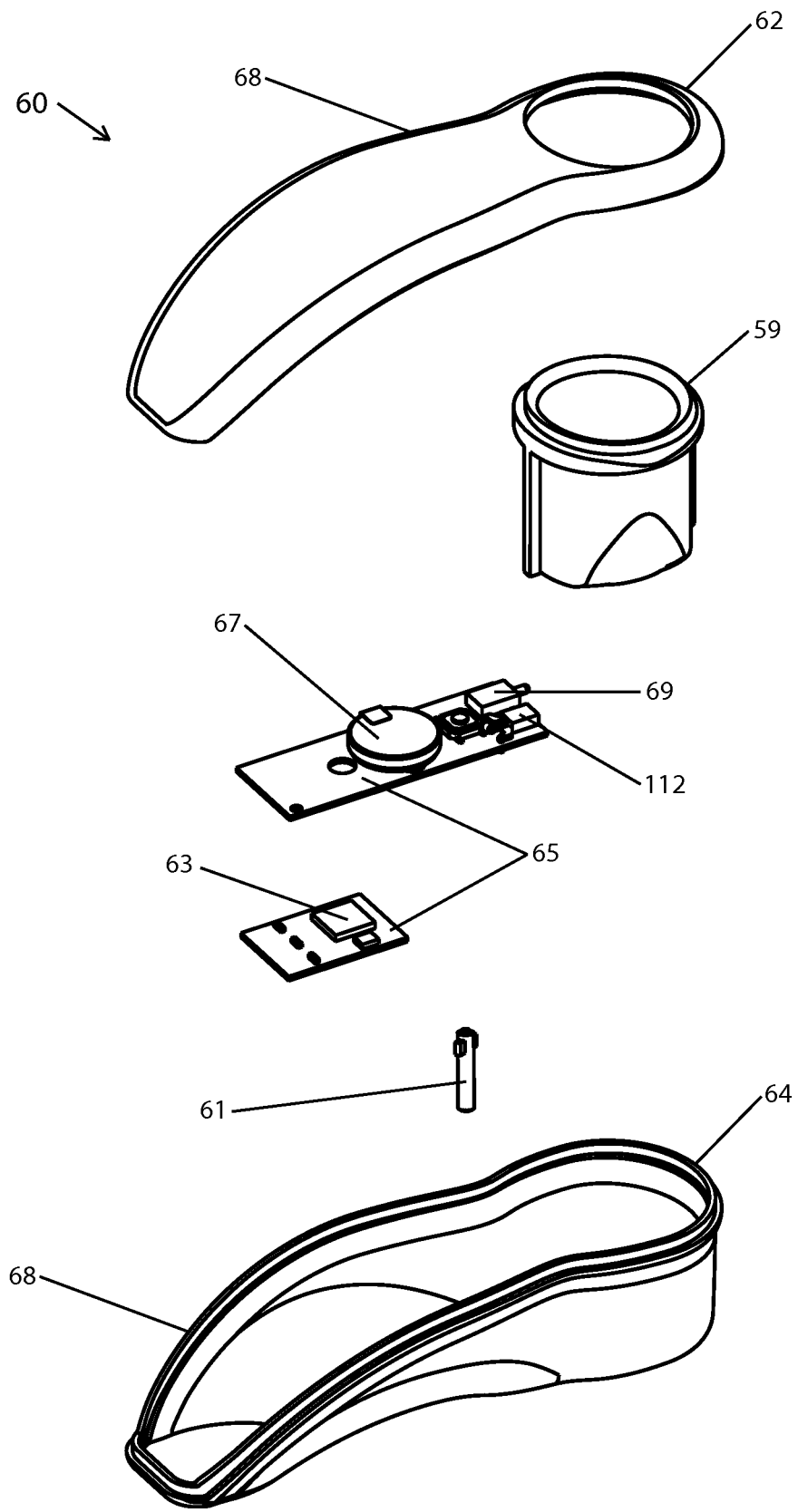
FIG. 10B is an exploded view of the embodiment of the collateral device shown in FIG. 10A.

FIG. 10A includes a further embodiment of the collateral device 60 shown in a perspective view with a medicament device 11 being received within an opening 66 of the collateral device 60. FIG. 10B is an exploded view of the collateral device embodiment 60. The embodiment of the collateral device 60 in FIGS. 10A-10B includes a handle portion 68, a top portion 62, and a bottom portion 64. The handle portion 68 may be used to facilitate use of the collateral device 60 and/or the medicament device 11 during an injection, for example. The medicament device 11 is receivable within the opening 66 of the collateral device 60, until the safety shield 15 traverses the collateral device opening 66 to contact the target area of a user as shown in the non-limiting embodiment of FIG. 10A.

The exploded view of FIG. 10B further provides a view of the components of the collateral device embodiment 60, including a light pipe 59, configured to direct light from the collateral device. The light may be provided on a printed circuit board assembly 65 of the collateral device 60 in a non-limiting embodiment. The light may include an LED in a further non-limiting embodiment. The light may provide a feedback to a user of the device during a use of the device 60. The light pipe 59 may direct the light upward through the opening 66 in the top housing 62 of the collateral device 60, in a non-limiting embodiment, such that it can be viewed by a user, for example.

A power source 67 may be further provided, and in one non-limiting embodiment, may be provided on the printed circuit board assembly 65. Other components may include a microprocessor, a storage module, other signal output components including a speaker, a display, an olfactory component or a vibratory component, in non-limiting embodiments. One or more sensors 69 may be provided in the collateral device embodiment 60 as described in detail herein. The sensor may include a contact sensor to detect contact with the medicament device when the medicament device is inserted into the collateral device 60. In one embodiment, the sensor 69 may include a contact switch as shown in FIG. 10B, wherein when the medicament device 11 is received within the opening 66, the contact switch is activated to indicate receipt of the medicament device 11 and correct positioning for medicament delivery, in a non-limiting embodiment. In another non-limiting embodiment, the sensor may further include an accelerometer which may identify status of the medicament device 11 as the medicament device is associated with the collateral device 60. The accelerometer may be used to identify a status of the device. The collateral device may further include a blue tooth transmitter 63 and a blue tooth pairing button to pair with and allow transfer of information between the collateral device 60 and other devices. The collateral device 60 may also include a microphone 112 wherein a status of the medicament device 11 may be determined based on the sounds received from the microphone 112 created by movement of the medicament device 11, or movement of components of the medicament device relative to one another during use of the device 11. Information about the status of the medicament device 11 may be provided to the user.

Figure 11A:
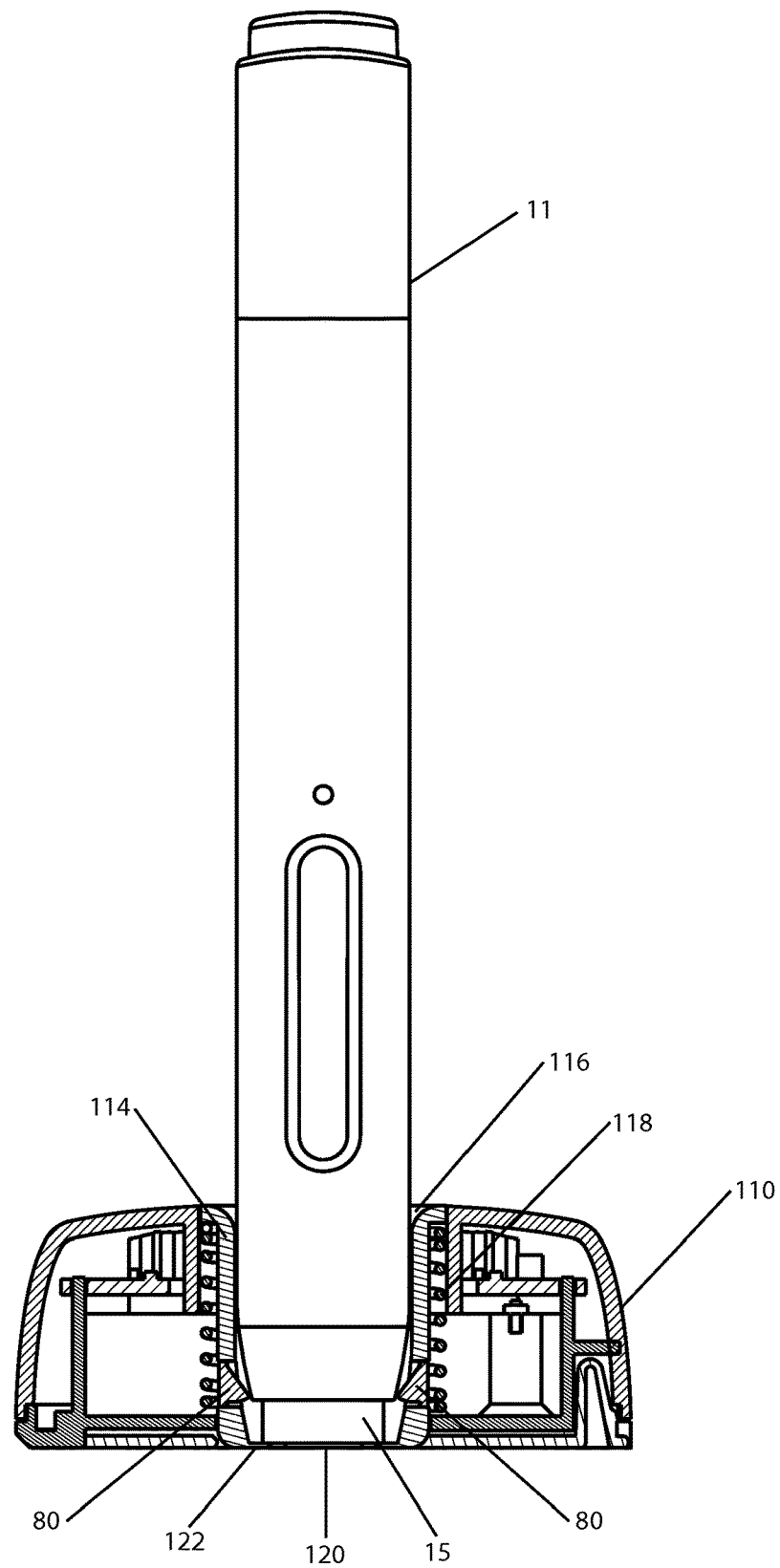
FIGS. 11A-C are side views of an embodiment of a system described herein, including a cross-sectional view of a further embodiment of a collateral device.
Figure 11B:
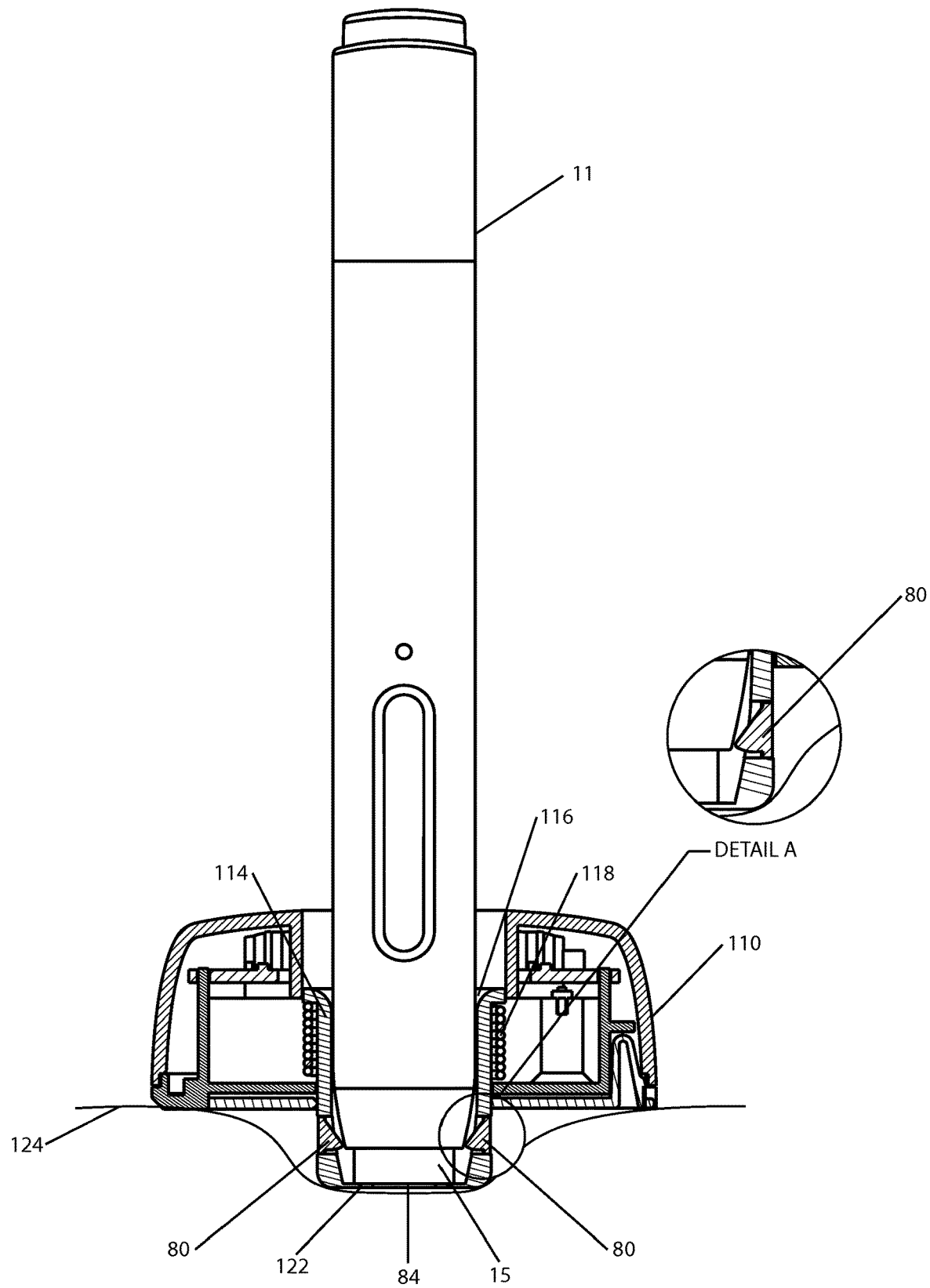
Figure 11C:
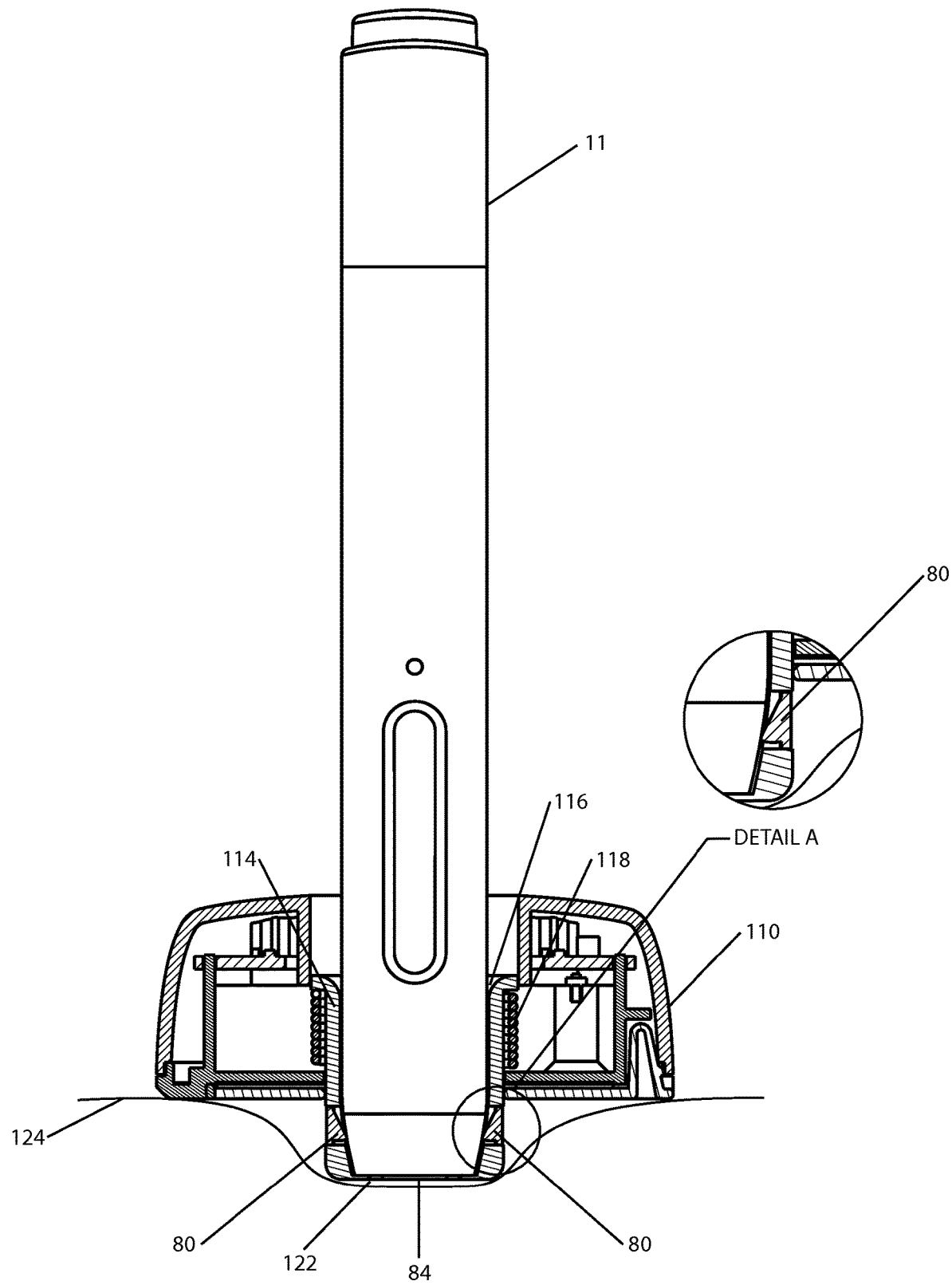

In a further embodiment, in FIG. 11A-C, a collateral device embodiment 110 including an internal element 114 having an opening 116 for receiving a medicament device, a biasing member 118, one or more sensors 80, and an aperture 120 for receiving an injection member of the medicament device 11 is provided. The internal element 114 is slidable relative to the collateral device housing 114, wherein when a bottom portion 122 of the collateral device is against a target area of a user, and a medicament device 11 is inserted into the opening 116 and pressed down toward the target area of the user, the biasing member 118 is deformed and the internal element 114 is displaced relative to the collateral device 110, such that it extends below the collateral device 110. Further movement of the medicament device toward the target area of the user as shown in FIG. 11C allows contact between a sensor 80 and a distal portion of the medicament device 11 when the safety shield 15 of the medicament device is depressed. Actuation of the medicament device 11 may occur following depression of the safety shield. Following delivery of medicament, pressure on the medicament device 11 may be released, and the biasing member 118 may retract the internal element 114 back into the collateral device. Further sensors may be provided between the portion of the collateral device and/or the internal element 114 that contacts the target area of the user to ensure contact there between during use of the device/system. This embodiment allows precise control of the start and stop position of the medicament device 11, and may provide for controlled movement of the medicament device and repeatable use of the sensors, by way of manipulation of the internal element 114. Control over the strength and resistance of the biasing member 118, among the other components of the embodiment may be further provided in this embodiment.

It should be borne in mind that all patents, patent applications, patent publications, technical publications, scientific publications, and other references referenced herein are hereby incorporated by reference in this application in order to more fully describe the state of the art to which the present invention pertains.

It is important to an understanding of the present invention to note that all technical and scientific terms used herein, unless defined herein, are intended to have the same meaning as commonly understood by one of ordinary skill in the art. The techniques employed herein are also those that are known to one of ordinary skill in the art, unless stated otherwise. For purposes of more clearly facilitating an understanding the invention as disclosed and claimed herein, the following definitions are provided.

While a number of embodiments of the present invention have been shown and described herein in the present context, such embodiments are provided by way of example only, and not of limitation. Numerous variations, changes and substitutions will occur to those of skill in the art without materially departing from the invention herein. For example, the present invention need not be limited to best mode disclosed herein, since other applications can equally benefit from the teachings of the present invention. Also, in the claims, means-plus-function and step-plus-function clauses are intended to cover the structures and acts, respectively, described herein as performing the recited function and not only structural equivalents or act equivalents, but also equivalent structures or equivalent acts, respectively. Accordingly, all such modifications are intended to be included within the scope of this invention as defined in the following claims, in accordance with relevant law as to their interpretation.

While one or more embodiments of the present invention have been shown and described herein, such embodiments are provided by way of example only. Variations, changes and substitutions may be made without departing from the invention herein. Accordingly, it is intended that the invention be limited only by the spirit and scope of the appended claims. The teachings of all references cited herein are incorporated in their entirety to the extent not inconsistent with the teachings herein.

What is claimed is:

1. A collateral device for use with one or more medicament devices, the collateral device comprising
   a collateral device housing comprising a top portion, a bottom portion for contacting a target surface, and an opening extending there between, the opening configured to receive a portion of the one or more medicament devices each comprising a medicament device housing and an actuation mechanism;
   at least a first sensor associated with the collateral device housing for detecting receipt of the portion of the medicament device into the opening;
   at least a second sensor associated with the collateral device housing for detecting actuation of the actuation mechanism of the medicament device, said second sensor comprising a microphone or a vibration sensor;
   a microprocessor; and
   a power source.

2. The collateral device of claim 1, wherein the first sensor comprises a contact sensor.

3. The collateral device of claim 1, wherein the collateral device is programmed to provide training and/or guidance.

4. The collateral device of claim 3, wherein when the collateral device provides training, the medicament delivery device does not include medicament.

5. The collateral device of claim 3, wherein when the collateral device provides guidance, the collateral device provides instructions while delivering medicament.

6. The collateral device of claim 1, further comprising a signal output component to provide a feedback, training and/or guidance to a user.

7. The collateral device of claim 1, further comprising a Smartphone configured to receive information from the collateral device, send information to the collateral device, provide feedback to a user, and/or provide feedback to the collateral device.

8. A collateral device for use with a medicament device, the collateral device comprising a collateral device housing comprising a top portion, a bottom portion, and an opening extending there between, the opening configured to receive a portion of the medicament device;
   at least a first sensor associated with the collateral device housing for detecting receipt of the portion of the medicament device into the opening;
   at least a second sensor associated with the collateral device housing for detecting actuation of an actuation mechanism of the medicament device, said second sensor comprising a microphone or a vibration sensor;
   a microprocessor;
   a power source, and
   a third sensor to detect contact of the bottom portion with a target surface.

* * * * *